United States Patent
Zhang et al.

(10) Patent No.: US 11,531,020 B2
(45) Date of Patent: Dec. 20, 2022

(54) METHODS AND COMPOSITIONS FOR NANOPORE SEQUENCING

(71) Applicants: YouHealth Biotech, Limited, Grand Cayman (KY); The Regents of the University of California, Oakland, CA (US)

(72) Inventors: Kang Zhang, San Diego, CA (US); Rui Hou, Shenyang (CN)

( * ) Notice: Subject to any disclaimer, the term of this patent is extended or adjusted under 35 U.S.C. 154(b) by 728 days.

(21) Appl. No.: 16/478,413

(22) PCT Filed: Jan. 17, 2018

(86) PCT No.: PCT/US2018/014021
§ 371 (c)(1),
(2) Date: Jul. 16, 2019

(87) PCT Pub. No.: WO2018/136495
PCT Pub. Date: Jul. 26, 2018

(65) Prior Publication Data
US 2021/0132032 A1    May 6, 2021

Related U.S. Application Data

(60) Provisional application No. 62/447,777, filed on Jan. 18, 2017.

(51) Int. Cl.
*G01N 33/487*  (2006.01)
*C07D 259/00*  (2006.01)
*C12Q 1/6869*  (2018.01)

(52) U.S. Cl.
CPC ..... *G01N 33/48721* (2013.01); *C07D 259/00* (2013.01); *C12Q 1/6869* (2013.01); *C12Q 2563/116* (2013.01); *C12Q 2565/607* (2013.01); *C12Q 2565/631* (2013.01)

(58) Field of Classification Search
CPC ............ C07D 259/00; G01N 33/48721; C12Q 1/6869; C12Q 2665/631
See application file for complete search history.

(56) References Cited

U.S. PATENT DOCUMENTS

| | | | |
|---|---|---|---|
| 5,504,182 A | 4/1996 | Cherdron et al. | |
| 2012/0039945 A1 | 2/2012 | Scott et al. | |
| 2015/0273389 A1* | 10/2015 | Liu ...................... | B01D 53/228 95/45 |
| 2018/0364214 A1* | 12/2018 | Maglia ................. | C12Q 1/6869 |
| 2019/0135866 A1* | 5/2019 | Gong ................... | C07D 259/00 |

FOREIGN PATENT DOCUMENTS

WO   WO-2013109827 A1   7/2013
WO   WO-2018136495 A1   7/2018

OTHER PUBLICATIONS

Ferguson et al. One-pot formation of large macrocycles with modifiable peripheries and internal cavities. Angew Chem Int Ed Engl 48(17):3150-3154 (2009).
Gong et al. Self-assembling organic nanotubes with precisely defined, sub-nanometer pores: formation and mass transport characteristics. Acc Chem Res 46(12):2856-2866 (2013).
Helsel et al. Highly conducting transmembrane pores formed by aromatic oligoamide macrocycles. J Am Chem Soc 130(47):15784-15785 (2008).
PCT/US2018/014021 International Preliminary Report on Patentability dated Aug. 1, 2019.
PCT/US2018/014021 International Search Report and Written Opinion dated Mar. 8, 2018.
Wei et al. Persistent Organic Nanopores Amenable to Structural and Functional Tuning. J Am Chem Soc 138(8):2749-2754 (2016).
Zhou et al. Self-assembling subnanometer pores with unusual mass-transport properties.Nat Commun 3:949 (2012).

* cited by examiner

*Primary Examiner* — Ethan C Whisenant
(74) *Attorney, Agent, or Firm* — Yong Chen

(57) ABSTRACT

Disclosed herein are methods and compositions relating to synthesized nanopores. The synthesized nanopores can be used for detecting a target molecule (e.g. RNA, DNA, or peptide).

19 Claims, 5 Drawing Sheets

METHODS AND COMPOSITIONS FOR NANOPORE SEQUENCING

CROSS-REFERENCE

This application claims the benefit of U.S. Provisional Application No. 62/447,777, filed Jan. 18, 2017, which application is incorporated herein by reference in its entirety.

BACKGROUND OF THE DISCLOSURE

Bacterial proteins having a structure that provides a hole on a nanometer scale are known as "nanopores." These nanopores may be employed to sequence biological polymers such as nucleic acids and proteins. For example, the nanopore may be placed in a membrane, with an applied voltage across the membrane potential, thereby creating a transmembrane potential that drives an electric current. This current can drive a charged molecule, such as a single-stranded DNA ("ssDNA"), through the nanopore. As the ssDNA passes through the nanopore, disruptions occur in the current that correspond to the nucleotides of the ssDNA. Each type of nucleotide, having its own unique structure, creates a signature disruption in the current. The readout of these current disruptions can be translated into a sequence. This process of sequencing DNA, RNA, and peptides with the use of nanopores is generally referred to as "nanopore sequencing."

SUMMARY OF THE DISCLOSURE

Disclosed herein, in certain embodiments, are methods of detecting a target molecule, the method comprising: contacting the target molecule with a membrane comprising a macrocycle nanopore, wherein the nanopore has a non-collapsible cavity; and measuring an electrical stimulus across the membrane, wherein transport of the target molecule causes a change in the electrical stimulus. In some embodiments, the nanopore is formed by aromatic compounds. In some embodiments, the nanopore is formed by oligohydrazides. In some embodiments, 2 or more nanopores are stacked together to form a nanotube. In some embodiments, formation of the nanotube is dependent on at least one of temperature, solvent, and concentration. In some embodiments, a diameter of a cavity of the nanopore is in a range of about 0.5 nm to about 3 nm. In some embodiments, a diameter of a cavity of the nanopore is about 2 nm. In some embodiments, the membrane is a lipid bilayer. In some embodiments, the lipid bilayer is from a cell. In some embodiments, the cell is a red blood cell. In some embodiments, the electrical stimulus is at least one of applied current and an applied voltage. In some embodiments, the target molecule is at least one of RNA, DNA, and a peptide. In some embodiments, the transport of the target molecule is through the cavity. In some embodiments, the transport of the target molecule is in proximity to the nanopore. In some embodiments, the transport of a subunit of the target molecule is measured. In some embodiments, the subunit of the target molecule is a nucleotide. In some embodiments, methods further comprise the step of generating a sequence of the target molecule. In some embodiments, the nanopore comprises at least one compound of Formula I:

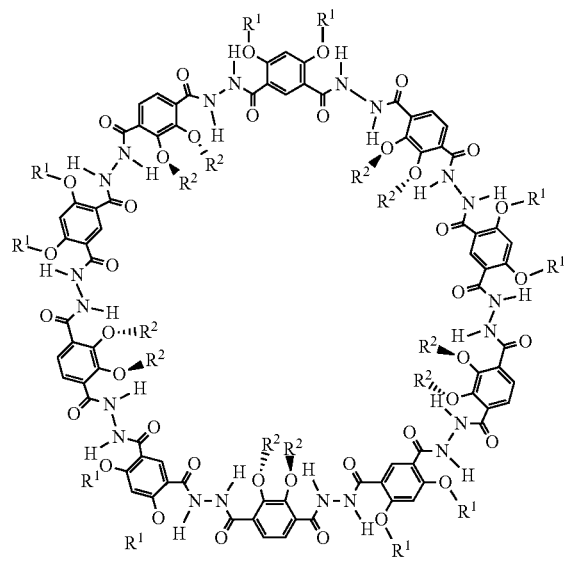

Formula I wherein:
$R^1$ is —$CH_2CH_2CH_2CH_3$; and
$R^2$ is —$CH_2CH_2$=$CH_3$ or —$(CH_2)_3S(CH_2)_4O(CH_2)_4O(CH_2)_4OH$.

Described herein, in certain embodiments, are methods for synthesizing a nanopore for use in detecting a target molecule, the method comprising: providing a reactant of Formula II; providing a reactant of Formula III; and combining the reactant of Formula II and the reactant of Formula III to yield a product of Formula I,

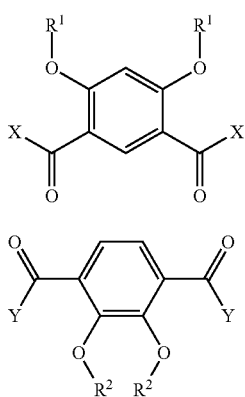

Formula II

Formula III

-continued

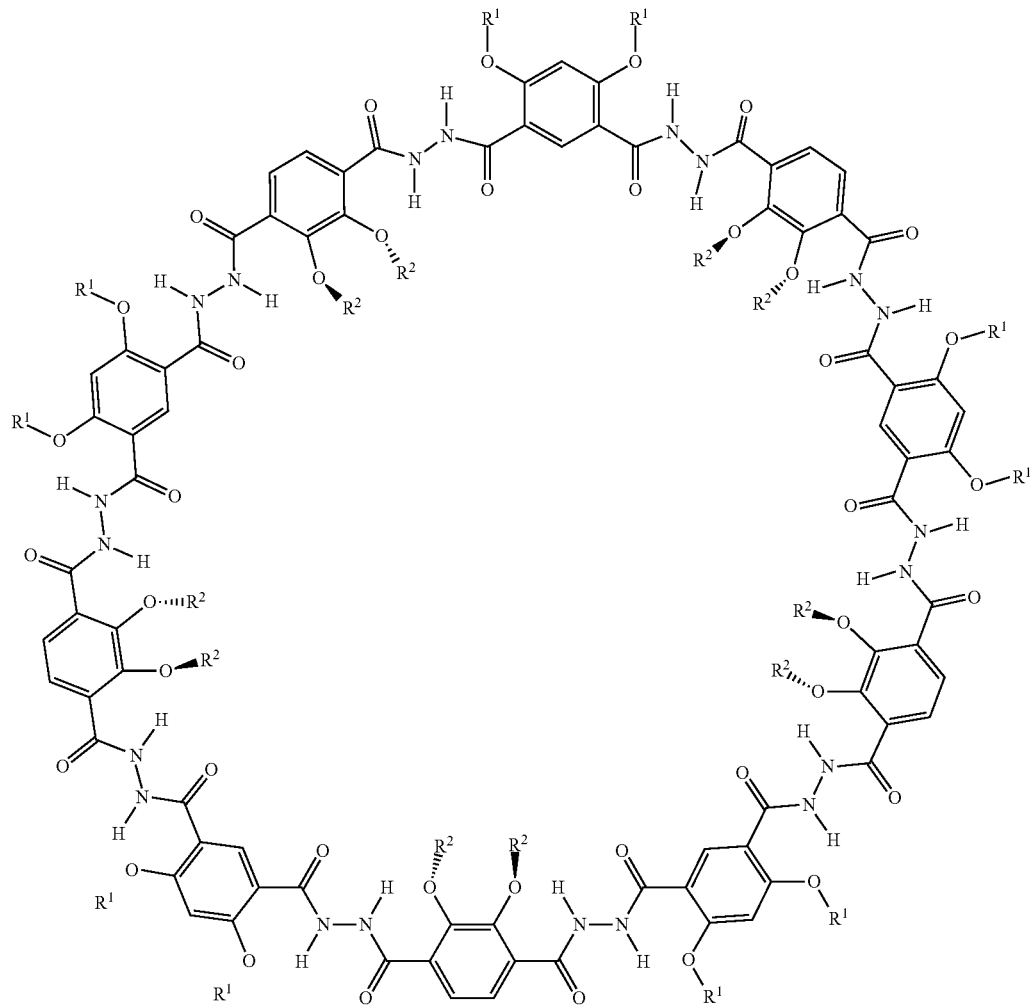

Formula I wherein:
R[1] is —CH$_2$CH$_2$CH$_2$CH$_3$;
X is Cl;
R[2] is —CH$_2$CH$_2$=CH$_3$ or —(CH$_2$)$_3$S(CH$_2$)$_4$O(CH$_2$)$_4$O(CH$_2$)$_4$OH;
Y is NHNH$_2$;
and wherein the product of Formula I is used for detecting a target molecule. In some embodiments, 2 or more nanopores are stacked together to form a nanotube. In some embodiments, formation of the nanotube is dependent on at least one of temperature, solvent, and concentration. In some embodiments, a diameter of a cavity of the nanopore is in a range of about 0.5 nm to about 3 nm. In some embodiments, a diameter of a cavity of the nanopore is about 2 nm. In some embodiments, the nanopore assembles in a membrane. In some embodiments, the membrane is a lipid bilayer. In some embodiments, the lipid bilayer is from a cell. In some embodiments, the cell is a red blood cell. In some embodiments, the target molecule is detected by applying an electrical stimulus. In some embodiments, the electrical stimulus is at least one of applied current and an applied voltage. In some embodiments, the target molecule is at least one of RNA, DNA, and a peptide. In some embodiments, a transport of the target molecule is through a cavity. In some embodiments, a transport of the target molecule is in proximity to the nanopore. In some embodiments, a subunit of the target molecule is detected. In some embodiments, the subunit of the target molecule is a nucleotide. In some embodiments, the methods further comprise the step of generating a sequence of the target molecule. In some embodiments, the nanopore comprises a cavity that is non-collapsible.

Disclosed herein, in certain embodiments, are methods of at least one of drug development screening, disease diagnosis, phylogenetic classification, parental and forensic identification, disease onset and recurrence, individual response to treatment versus population bases, and monitoring of therapy using any of the methods described herein.

Disclosed herein, in certain embodiments, are methods of sequencing the target molecule at point of care using any one of the preceding claims.

Disclosed herein, in certain embodiments, are compositions comprising a nanopore of Formula I, wherein Formula I is Formula I

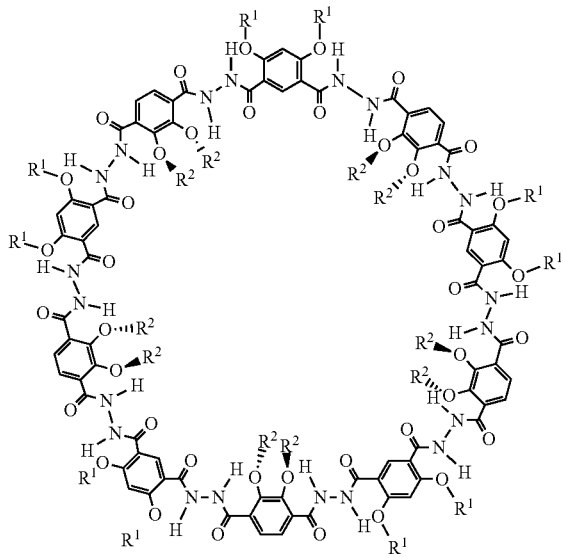

wherein:
R[1] is —CH$_2$CH$_2$CH$_2$CH$_3$;
R[2] is —CH$_2$CH$_2$=CH$_3$ or —(CH$_2$)$_3$S(CH$_2$)$_4$O(CH$_2$)$_4$O(CH$_2$)$_4$OH;
and a membrane. In some embodiments, 2 or more nanopores are stacked together to form a nanotube. In some embodiments, formation of the nanotube is dependent on at least one of temperature, solvent, and concentration. In some embodiments, a diameter of a cavity of the nanopore is in a range of about 0.5 nm to about 3 nm. In some embodiments, a diameter of a cavity of the nanopore is about 2 nm. In some embodiments, the membrane is a lipid bilayer. In some embodiments, the lipid bilayer is from a cell. In some embodiments, the cell is a red blood cell.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1:
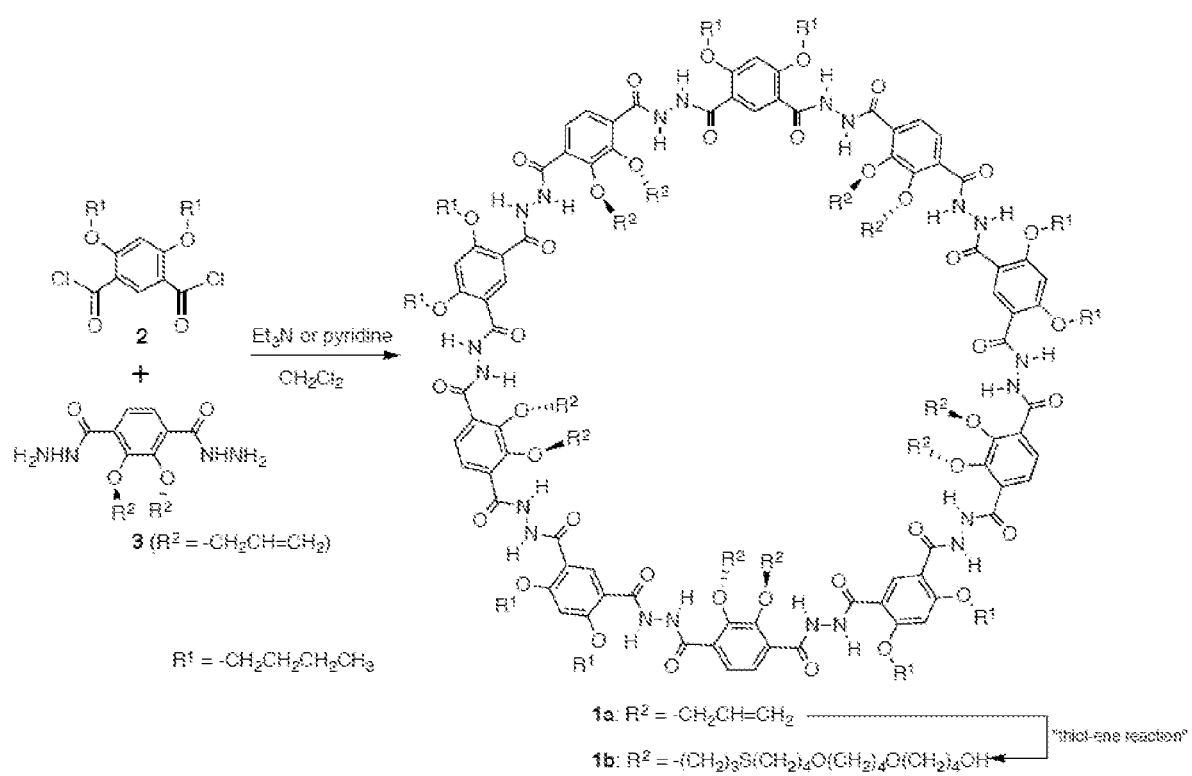
FIG. 1 depicts synthesis and design of a nanopore ring.

Sequencing of molecules such as nucleic acids is an indispensable technique in medical and biological applications. Information obtained from nucleic acids can be helpful in diagnosing and/or treating a subject. For example, the nucleic acid sequence of a subject can be used to identify, diagnose, and potentially develop treatments for genetic diseases.

There are various methods available that can be used to sequence a target molecule. Such methods, however, are expensive and time consuming and may not provide accurate sequence information. Sequencing techniques involving nanopores have the potential to quickly and inexpensively sequence nucleic acids. However, there still exist technological limitations using nanopore sequencing including resolution, structural regularity, and tunability of the nanopore. Provided herein are methods and compositions relating to synthesized nanopores that address these issues.

Certain Terminologies

Unless otherwise defined, all technical terms used herein have the same meaning as commonly understood by one of ordinary skill in the art to which this invention belongs.

As used herein, the term "comprising" and its grammatical equivalents specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

As used herein, the singular form "a", "an" and "the" include plural references unless the context clearly dictates otherwise.

The term "nucleic acid," as used herein, refers to a molecule comprising one or more nucleic acid subunits. A nucleic acid can include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). In some examples, a nucleic acid is deoxyribonucleic acid (DNA) or ribonucleic acid (RNA), or derivatives thereof. A nucleic acid can be a synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. A nucleic acid can be single-stranded or double stranded.

The term "subject" as used herein includes any member of the animal kingdom, including humans.

Nanopores

Described herein, in some embodiments, are synthesized nanopores. In some instances, nanopores disclosed herein comprise a macrocycle. In some instances, nanopores are at least one of aromatic, non-aromatic, heteroaromatic, and bicyclic aromatic. In some cases, nanopores disclosed herein are aromatic. In some cases, synthesized nanopores disclosed herein are organic macrocycles. In some instances, nanopores disclosed herein are oligohydrazide macrocycles. In some instances, nanopores disclosed herein comprise an oligohydrazide macrocycle comprising a rigid backbone.

Nanopores can comprise at least one residue. In some instances, the at least one residue is a hydrocarbon. In some instances, the hydrocarbon is a saturated hydrocarbon. The hydrocarbon can be an unsaturated hydrocarbon. Non-limiting examples of unsaturated hydrocarbon include substituted or unsubstituted alkenes, including but not limited to, ethylene, chloro ethylene, bromo ethylene, iodo ethylene, propylene, chloro propylene, hydroxyl propylene, 1-butylene, 2-butylene (cis or trans), isobutylene, 1,3-butadiene, pentylene, hexene, cyclopropylene, cyclobutylene, cyclohexene, benzene, and toluene. Unsaturated hydrocarbons can include all the isomeric forms of unsaturation, such as, but not limited to, cis and trans isomers, E and Z isomers, and positional isomers. In some instances, nanopores comprise benzene residues.

In some instances, nanopores are macrocycles comprising linked residues. In some instances, nanopores are macrocycles comprising meta-linked residues. Nanopores in some cases are macrocycles comprising para-linked residues. In some instances, nanopores are macrocycles comprising a combination of meta- and para-linked residues. In some cases, nanopores are macrocycles comprising alternating meta- and para-linked residues.

In some instances, at least one of meta- and para-linked affects a structure of a macrocycle. In some instances, alternating meta- and para-linked residues result in a macrocycle with at least one of a convex and a concave edge. In some cases, alternating meta- and para-linked residues result in a macrocycle that is planar.

In some instances, nanopores comprise hydrogen-bonding side chains. Hydrogen-bonding side chains can enforce stacking of nanopores. In some instances, hydrogen-bonding side chains promote self-assembly of nanopores into nanopore tubes. In some instances, nanopores that are stackable are non-collapsible.

An exemplary macrocycle as described herein has Formula I. In some instances, $R^1$ is —$CH_2CH_2CH_2CH_3$. In some instances, $R^2$ is —$CH_2CH_2$=$CH_3$. In some instances, $R^2$ is an amphipathic alpha-helix. For example, the amphipathic alpha-helix is an alpha-helix with one side or surface being hydrophilic and a second side or surface being hydrophobic. In some instances, the alpha-helix is designed by choosing an amino acid sequence of the corresponding oligopeptides. In some cases, the macrocycle of Formula I is a stereoisomer, diastereomer, or enantiomer represented by any of the structures shown herein. In some instances, the macrocycle of Formula I is a mixture of stereoisomers, diastereomers, or enantiomers represented by any of the structures shown herein. In some instances, the macrocycle of Formula I is a racemate of the stereoisomer represented by any of the structures herein.

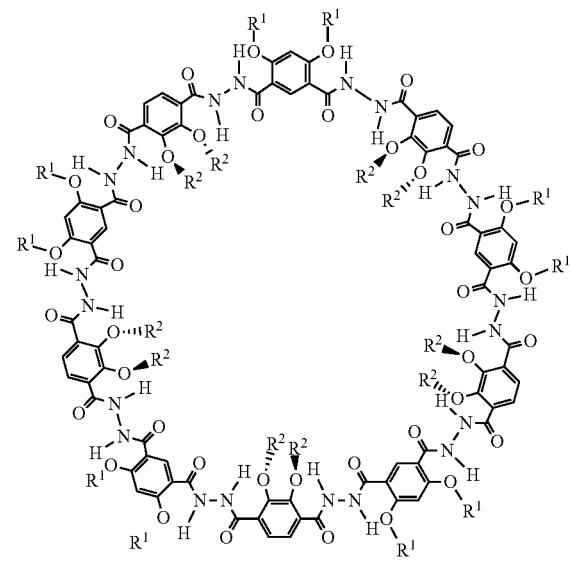

Formula I

In some instances, nanopores comprise a functional group. Exemplary functional groups include, but not limited to, carboxylic acid or salts thereof, amino, mercapto, azido, aldehyde, ester, hydroxyl, carbonyl, sulfate, sulfonate, phosphate, cyanate, succinimidyl ester, oxo, amino, nitrile, nitro, hydroxyl, alkyl, alkylene, alkynyl, alkoxy, aryl, cycloalkyl, heterocyclyl, heteroaryl, allyl, or substituted derivatives thereof. In some cases, nanopores comprise an alkyl group such as, but not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl, hexyl, and longer alkyl groups, such as heptyl, octyl, and the like. In some instances, nanopores are synthesized with specific recognition sequences. In some instances, the at least one functional group is introduced via at least one of an ester linkage, an amide linkage, a carbamate linkage, an ether linkage, an acetal linkage, and an amine linkage.

In some cases, a nanopore comprises a functional group that points inward of a nanopore cavity. In some instances, a nanopore comprises at least 1, 2, 3, 4, 5, 6, 7, 8, 9, 10, 11, 12, 13, 14, 15, 16, 17, 18, 19, 20, or more than 20 functional groups that point inward of a nanopore cavity. In some instances, a nanopore comprises at most 1, 2, 3, 4, 5, 6, 7, 8, 9, 10, 11, 12, 13, 14, 15, 16, 17, 18, 19, 20, or more than 20 functional groups that point inward of a nanopore cavity. In some instances, the functional group is the same. The functional group can be different. In some cases, the functional group is chosen to result in a nanopore with a specified diameter. In some instances, a diameter of a nanopore cavity is tunable based on the functional group.

Nanopores as described herein can be synthesized to have a specified diameter. In some instances, nanopores have an inner cavity diameter of about 2.0 (nanometer) nm. In some instances, nanopores have an inner cavity diameter at most 0.25 nm, 0.5 nm, 0.75 nm, 1.5 nm, 1.75 nm, 2.0 nm, 2.25 nm, 2.5 nm, 2.75 nm, 3 nm, or more than 3 nm. In some instances, nanopores have an inner cavity diameter of at least 0.25 nm, 0.5 nm, 0.75 nm, 1.5 nm, 1.75 nm, 2.0 nm, 2.25 nm, 2.5 nm, 2.75 nm, 3 nm, or more than 3 nm.

In some instances, nanopores as described herein have a height of about 5 um to about 10 um. In some instances, nanopores have a height of at least 1 um, 2 um, 3 um, 4 um, 5 um, 6 um, 7 um, 8 um, 9 um, 10 um, 11 um, 12 um, 13 um, 14 um, 15 um, 16 um, 17 um, 18 um, 19 um, 20 um, or more than 20 um. In some instances, nanopores have a height of at most 1 um, 2 um, 3 um, 4 um, 5 um, 6 um, 7 um, 8 um, 9 um, 10 um, 11 um, 12 um, 13 um, 14 um, 15 um, 16 um, 17 um, 18 um, 19 um, 20 um, or more than 20 um.

Nanopores can be stacked to form a nanotube. In some instances, at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 85 100, 125, 150, 175, 200, 225, 250, 275, 300, or more than 300 nanopores are stacked to form the nanotube. In some instances, up to 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 85 100, 125, 150, 175, 200, 225, 250, 275, 300, or more than 300 are stacked to form the nanotube. In some cases, the nanotube has a height of about 4 nm. In some cases, the nanotube has a height of about 4 to about 10 nm. In some instances, the nanotube has a height of at least 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, or more than 20 nm. In some cases, the nanotube has a height of at most 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, or more than 20 nm.

In some cases, multiple nanotubes form a nanotube array. In some instances, at least 1, 2, 3, 4, 5, 6, 7, 8, 9, 10, or more than 10 nanotubes form the nanotube array. In some instances, up to 1, 2, 3, 4, 5, 6, 7, 8, 9, 10, or more than 10 nanotubes form the nanotube array.

Methods of Synthesizing Nanopores

Described herein, in certain embodiments, are methods for synthesizing nanopores in a one-pot reaction. In some instances, reactions are carried out in a one-pot. Methods for synthesizing nanopores in a one-pot reaction can be efficient. In some cases, the one-pot reaction results in high yield. In some instances, reactions are carried out using "click" chemistry.

In some instances, a one-pot reaction involves a reactant of Formula II. In some instances, $R^1$ is —$CH_2CH_2CH_2CH_3$. In some cases, X is Cl. In some cases, the reactant of Formula II is a stereoisomer, diastereomer, or enantiomer represented by any of the structures shown herein. In some instances, the reactant of Formula II is a mixture of stereoisomers, diastereomers, or enantiomers represented by any of the structures shown herein. In some instances, the reactant of Formula II is a racemate of the stereoisomer represented by any of the structures herein.

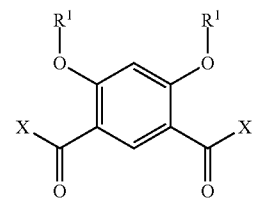

Formula II

In some instances, a one-pot reaction involves a reactant of Formula III. In some instances, $R^2$ is —$CH_2CH_2=CH_3$. In some instances, $R^2$ is an amphipathic alpha-helix. For example, the amphipathic alpha-helix is an alpha-helix with one side or surface being hydrophilic and a second side or surface being hydrophobic. In some instances, the alpha-helix is designed by choosing an amino acid sequence of the corresponding oligopeptides. In some instances, Y is $NHNH_2$. In some cases, the reactant of Formula III is a stereoisomer, diastereomer, or enantiomer represented by any of the structures shown herein. In some instances, the reactant of Formula III is a mixture of stereoisomers, diastereomers, or enantiomers represented by any of the structures shown herein. In some instances, the reactant of Formula III is a racemate of the stereoisomer represented by any of the structures herein.

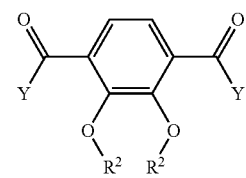

Formula III

In some instances, a reaction involves a reactant of Formula II and a reactant of Formula III. The reaction may be performed with at least one of acetone, toluene, chlorobenzene, methylene chloride, ethylene dichloride, dioxane, tetrahydrofuran (THF), tert-butyl methyl ether, diisopropyl ether, 1,2-dimethoxyethane (glyme), acetonitrile, water, and a mixture thereof as the solvent. In some instances, the reaction is with methylene chloride ($CH_2Cl_2$).

In some instances, a reaction time is about 30 seconds, 1 minute, 5 minutes, 10 minutes, 30 minutes, 1 hour, 2 hours, 3 hours, 4 hours, 5 hours, 10 hours, 20 hours, 30 hours, 40 hours, 50 hours, 60 hours, 70 hours, 80 hours, 90 hours, and 100 hours. In some instances, a reaction time is at most 30 seconds, 1 minute, 5 minutes, 10 minutes, 30 minutes, 1 hour, 2 hours, 3 hours, 4 hours, 5 hours, 10 hours, 20 hours, 30 hours, 40 hours, 50 hours, 60 hours, 70 hours, 80 hours, 90 hours, and 100 hours. In some instances, a reaction time is at least 30 seconds, 1 minute, 5 minutes, 10 minutes, 30 minutes, 1 hour, 2 hours, 3 hours, 4 hours, 5 hours, 10 hours, 20 hours, 30 hours, 40 hours, 50 hours, 60 hours, 70 hours, 80 hours, 90 hours, and 100 hours.

In some cases, a reaction is at about room temperature. A reaction temperature may be about −20° C., −10° C., 0° C., 10° C., 20° C., 30° C., 40° C., 50° C., 60° C., 70° C., 80° C., 90° C., 100° C., 110° C., 120° C., 130° C., 140° C., 150° C., or more than 150° C. In some cases, a reaction temperature is at least −20° C., −10° C., 0° C., 10° C., 20° C., 30° C., 40° C., 50° C., 60° C., 70° C., 80° C., 90° C., 100° C., 110° C., 120° C., 130° C., 140° C., 150° C., or more than 150° C. In some cases, a reaction temperature is at most −20° C., −10° C., 0° C., 10° C., 20° C., 30° C., 40° C., 50° C., 60° C., 70° C., 80° C., 90° C., 100° C., 110° C., 120° C., 130° C., 140° C., 150° C., or more than 150° C.

In some instances, nanopores described herein are analyzed by at least one of column chromatography, optical rotation, capillary electrophoresis, circular dichroism, mass spectroscopy, X-ray crystallography, fluorescence spectroscopy, atomic force microscopy, and nuclear magnetic resonance (NMR) spectroscopy.

Nanopore Systems

Provided herein are systems comprising nanopores described herein and a membrane. The membrane may be any membrane suitable for insertion of a nanopore described herein. In some instances, the membrane is at least one of an organic membrane and an inorganic membrane. An exemplary membrane is a lipid bilayer. A lipid bilayer generally comprises two layers of phospholipids with the hydrophobic tails of the two layers facing each other. In some instances, the membrane is hydrophobic. In some instances, the membrane is hydrophilic. The membrane can comprise hydrophobic portions (e.g., the tails of phospholipids facing the inside of a lipid bilayer) and hydrophilic portions (e.g., the phospholipid heads facing the outside of a lipid bilayer).

In some cases, a membrane is a synthetic membrane. The synthetic membrane may be formed of a polymeric material. In some instances, the synthetic membrane comprises lipids such as phosphatidylcholine, sphingomyelin, phosphatidylethanolamine, phosphoinositol, phosphatidylserine, and sterols.

In some instances, a membrane is a lipid bilayer from a cell. The cell can be a eukaryotic cell. In some instances, the cell is a red blood cell (RBC). In some instances, the membrane is an artificial cellular membrane.

In some instances, nanopores self-assemble in a membrane. In some instances, at least one of concentration, temperature, and solvent affects self-assembly of the nanopores. For example, depending whether the solvent is polar or non-polar can affect the size of the nanopores that self-assemble. A solvent can be at least one of an aprotic solvent, a protic solvent, a polar solvent, a non-polar solvent, and an ionic solvent. Exemplary solvents include, but not limited to, a halogenated solvent, a chlorinated solvent, dichloromethane, dichloroethane, tetrachloroethane, chloroform, tetrachloromethane, trichloroethane, hexane, benzene, toluene, 1,4-dioxane, diethyl ether, tetrahydrofuran, ethyl acetate, acetone, dimethylformamide, acetonitrile, dimethyl sulfoxide, n-butanol, isopropanol, n-propanol, ethanol, methanol, water, formic acid, acetic acid, and trifluoroacetic acid.

Nanopores, in some instances, self-assemble in a membrane at 37° C. In some instances, nanopores self-assemble in the membrane at least at −20° C., −4° C. −10° C., 0° C., 5° C., 10° C., 15° C., 20° C., 25° C., 30° C., 35° C., 40° C., 45° C., 50° C., 55° C., 60° C., 65° C.,70° C., 75° C., 80° C., 85° C., 90° C., 95° C., 100° C., or more than 100° C. In some instances, nanopores self-assemble in the membrane at most at −20° C., −4° C. −10° C., 0° C., 5° C., 10° C., 15° C., 20° C., 25° C., 30° C., 35° C., 40° C., 45° C., 50° C., 55° C., 60° C., 65° C.,70° C., 75° C., 80° C., 85° C., 90° C., 95° C., 100° C., or more than 100° C. Nanopores can self-assemble in a membrane at about −20° C., −4° C. -10° C., 0° C., 5° C., 10° C., 15° C., 20° C., 25° C., 30° C., 35° C., 40° C., 45° C., 50° C., 55° C., 60° C., 65° C.,70° C., 75° C., 80° C., 85° C., 90° C., 95° C., 100° C., or more than 100° C.

In some instances, a concentration of nanopores that assembles in a membrane such as a RBC membrane is 10 uM. In some instances, the concentration of nanopores that assembles in a membrane is 5 uM. The concentration of nanopores that assembles in a membrane can be at least 1 uM, 2 uM, 3 uM, 4 uM, 5 uM, 6 uM, 7 uM, 8 uM, 9 uM, 10 uM, 11 uM, 12 uM, 13 uM, 14 uM, 15 uM, 16 uM, 17 uM, 18 uM, 19 uM, 20 uM, or more than 20 uM. In some instances, the concentration of nanopores that assembles in a membrane is about 1 uM, 2 uM, 3 uM, 4 uM, 5 uM, 6 uM, 7 uM, 8 uM, 9 uM, 10 uM, 11 uM, 12 uM, 13 uM, 14 uM, 15 uM, 16 uM, 17 uM, 18 uM, 19 uM, 20 uM, or more than 20 uM. In some instances, the concentration of nanopores that assembles in a membrane is at most 1 uM, 2 uM, 3 uM, 4 uM, 5 uM, 6 uM, 7 uM, 8 uM, 9 uM, 10 uM, 11 uM, 12 uM, 13 uM, 14 uM, 15 uM, 16 uM, 17 uM, 18 uM, 19 uM, 20 uM, or more than 20 uM. In some instances, the concentration of nanopores is at most 1 uM, 2 uM, 3 uM, 4 uM, 5 uM, 6 uM, 7 uM, 8 uM, 9 uM, 10 uM, 11 uM, 12 uM, 13 uM, 14 uM, 15 uM, 16 uM, 17 uM, 18 uM, 19 uM, 20 uM, or more than 20 uM.

A membrane has any suitable thickness for insertion of a nanopore. In some instances, the membrane has a suitable thickness for detecting a target molecule. In some embodiments, the membrane is about 1 nm, 2 nm, 3 nm, 4 nm, 5 nm, 6 nm, 7 nm, 8 nm, 9 nm, 10 nm, 15 nm, 20 nm, 25 nm, 30 nm, 50 nm, 100 nm, 200 nm, 300 nm, 400 nm, 500 nm, 1000 nm, 2000 nm, 4000 nm, 6000 nm, 8000 nm, 10000 nm, 15000 nm, 20000 nm, 25000 nm, 30000 nm, or more than 30000 nm thick. In some instances, the membrane is at most 1 nm, 2 nm, 3 nm, 4 nm, 5 nm, 6 nm, 7 nm, 8 nm, 9 nm, 10 nm, 15 nm, 20 nm, 25 nm, 30 nm, 50 nm, 100 nm, 200 nm, 300 nm, 400 nm, 500 nm, 1000 nm, 2000 nm, 4000 nm, 6000 nm, 8000 nm, 10000 nm, 15000 nm, 20000 nm, 25000 nm, 30000 nm, or more than 30000 nm thick.

In some instances, a membrane for insertion of a nanopore has a length of 60 um. The membrane for insertion of the nanopore may have a length of at least 10 um, 15 um, 20 um, 25 um, 30 um, 35 um, 40 um, 45 um, 50 um, 55 um, 60 um, 65 um, 70 um, 75 um, 80 um, 85 um, 90 um, 95 um, 100 um, or more than 100 um. In some instances, the membrane for insertion of the nanopore has a length of at most 10 um, 15 um, 20 um, 25 um, 30 um, 35 um, 40 um, 45 um, 50 um, 55 um, 60 um, 65 um, 70 um, 75 um, 80 um, 85 um, 90 um, 95 um, 100 um, or more than 100 um.

Figure 2:
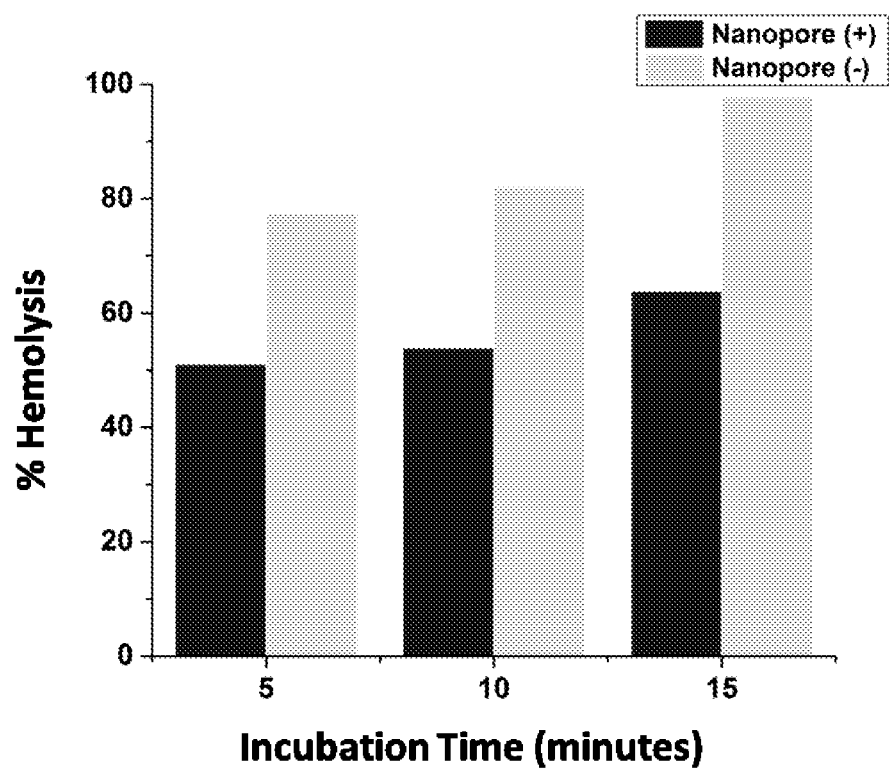
FIG. 2 depicts a graph of percent hemolysis on the Y axis versus incubation time (minutes) of red blood cells (RBCs) on the X axis with and without a nanopore.
Figure 3:
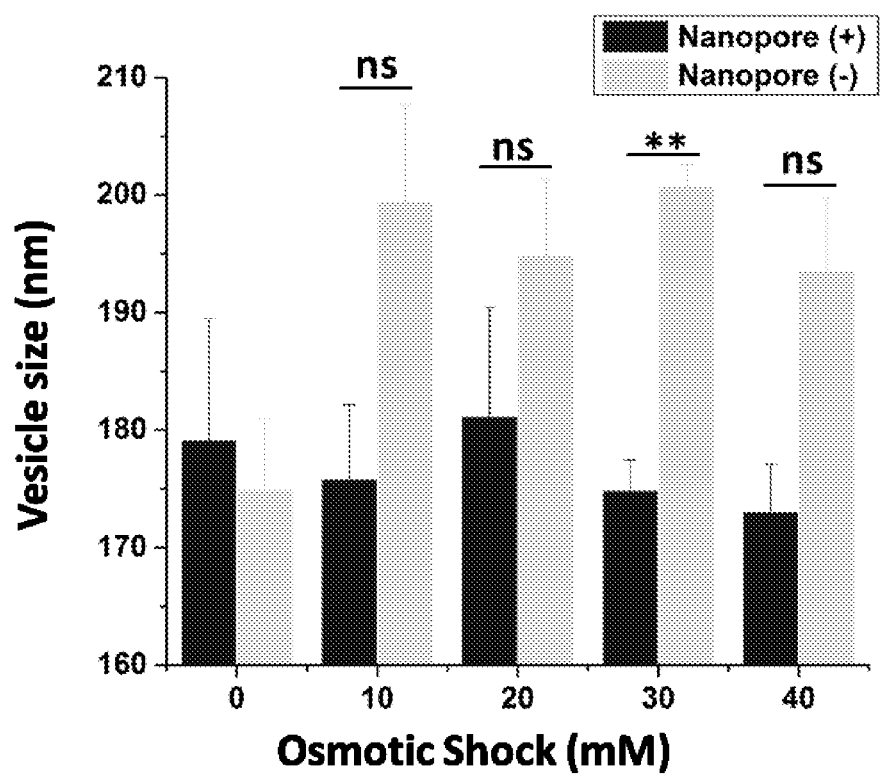
FIG. 3 depicts a graph of vesicle swelling of RBCs vesicle size incubated with and without a nanopore. Vesicle size (nm) of RBCs is depicted on the Y axis versus osmotic shock (mM) on the X axis. ** indicate significance and "ns" refers to "not significant."
Figure 4A:
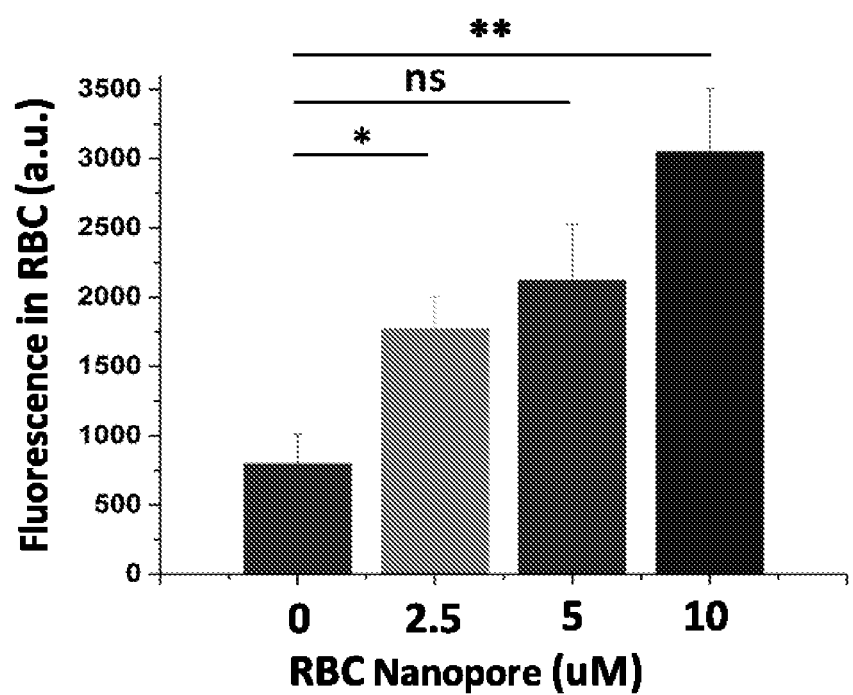
FIGS. 4A-4B depict graphs of fluorescence in RBCs on the Y axis versus concentration of nanopore (uM) on the X axis. RBCs were incubated with Ciprofloxacin (FIG. 4A) or Rhodamine B (FIG. 4B). * and ** indicate significance and "ns" refers to "not significant."
Figure 4B:
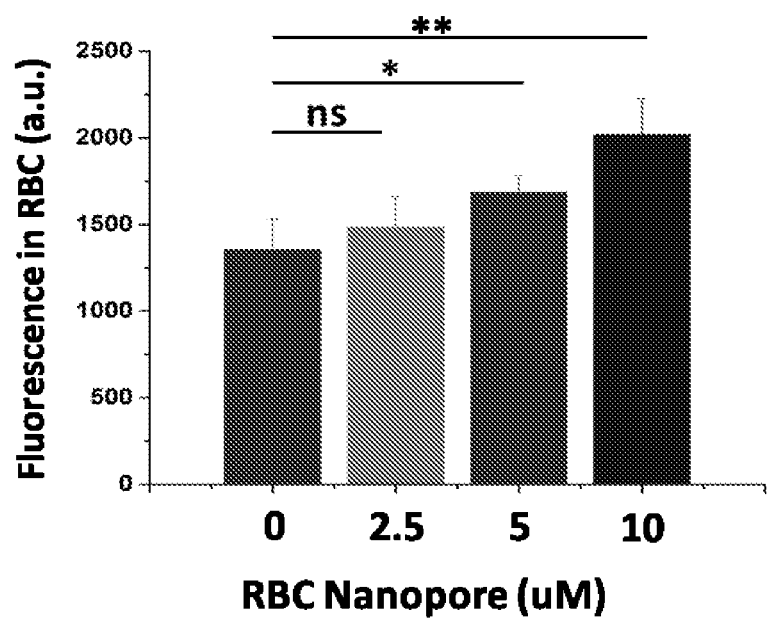

In some instances, nanopores exhibit at least one of improved selectivity, affinity, and ion transport. For example, in instances of osmotic shock, nanopores can protect RBCs from swelling by facilitating ion transport. Referring to FIG. 2 and FIG. 3, suspensions of RBCs and nanopores exhibit reduced percentage of hemolysis and vesicle size than suspensions of RBCs alone. In some instances, nanopores permit faster transport of a molecule across a membrane. In some instances, transport of small molecules can be facilitated by nanopores (e.g., as seen in FIGS. 4A-4B).

Methods of Sequencing with Nanopores

Provided herein are methods of sequencing biological molecules (e.g., nucleic acids, peptides) with nanopores disclosed herein. In some instances, the methods comprise use of synthesized nanopores disclosed herein for sequencing a target molecule. Target molecules disclosed herein may be at least one of RNA, DNA, and a peptide. In some instances, at least one of RNA and DNA that is sequenced is single stranded. In some instances, at least one of RNA and DNA that is sequenced is double stranded. In some instances, a target molecule comprises a portion of a genome of a cell such as an intron, regulatory region, allele, variant, or a mutation.

Provided herein are methods of sequencing a target molecule with a nanopore disclosed herein, wherein the target molecule comprises RNA. The target molecule may comprise fragmented RNA. The target molecule may comprise partially degraded RNA. The target molecule may comprise a microRNA or portion thereof. The target molecules may comprise an RNA molecule or a fragmented RNA molecule (RNA fragments) selected from: a microRNA (miRNA), a pre-miRNA, a pri-miRNA, a mRNA, a pre-mRNA, a viral RNA, a viroid RNA, a virusoid RNA, circular RNA (circRNA), a ribosomal RNA (rRNA), a transfer RNA (tRNA), a pre-tRNA, a long non-coding RNA (lncRNA), a small nuclear RNA (snRNA), a circulating RNA, a cell-free RNA, an exosomal RNA, a vector-expressed RNA, an RNA transcript, a synthetic RNA, and combinations thereof.

Provided herein are methods of sequencing a target molecule with a nanopore disclosed herein, wherein the target molecule comprises DNA. The target molecule may comprise DNA. The target molecule may comprise a denatured DNA molecule or fragment thereof. The target molecule may comprise DNA selected from: genomic DNA, viral DNA, mitochondrial DNA, plasmid DNA, amplified DNA, circular DNA, circulating DNA, cell-free DNA, or exosomal DNA. The DNA may be single-stranded DNA (ssDNA), double-stranded DNA, denaturing double-stranded DNA, synthetic DNA, and combinations thereof. The circular DNA may be cleaved or fragmented.

Provided herein are methods comprising detecting target molecules upon the passage through a nanopore disclosed herein or in proximity to a nanopore disclosed herein. In some instances, a subunit of the target molecule is detected upon the passage through or in proximity to a nanopore. For example, a nucleotide of a nucleic acid is detected upon the passage through or in proximity to a nanopore. In some instances, a signal is detected upon passage through or in proximity to a nanopore of a target molecule. The signal can be an electrical signal that is generated upon the passage of a target molecule through or in proximity to a nanopore. The nanopore can be disposed adjacent or in proximity to a sensing circuit or an electrode coupled to a sensing circuit, such as, for example, a complementary metal-oxide semiconductor (CMOS) or field effect transistor (FET) circuit.

In some instances, methods disclosed herein comprise sequencing a target molecule by applying an electrical stimulus across a membrane comprising a nanopore as disclosed herein. The electrical stimulus can be various electrical stimuli. Non-limiting examples of electrical stimulus include an applied current and an applied voltage. The current can be at least one of a direct current (DC) and an alternating current (AC). The electrical stimulus can constitute a series of electrical pulses. In some instances, the membrane comprising a nanopore includes at least one of a trans side and a cis side. In some instances, a target molecule is detected as it transports from the cis side to the trans side following application of the electrical stimulus.

In some cases, a membrane comprising a nanopore as disclosed herein is formed on a partition. The partition may comprise at least one of a cis side and a trans side. The partition may be at least one of an organic material and inorganic material. For example, the partition is made of organic polymers, inorganic polymers such as plastic or polyamide, or insulating material. In some instances, the partition is at least 5 um, 10 um, 15 um, 20 um, 25 um, 30 um, 35 um, 40 um, 45 um, 50 um, or more than 50 um thick.

In some instances, applying the electrical stimulus to the membrane occurs via an electrode. In some instances, voltage is in a range of about 10 mV to about 1000 mV, about 100 mV to about 500 mV, about 200 mV to about 400 mV. In some instances, voltage is at least 10 mV, 20 mV, 30 mV, 40 mV, 50 mV, 60 mV, 70 mV, 80 mV, 90 mV, 100 mV, 125 mV, 150 mV, 175 mV, 200 mV, 225 mV, 250 mV, 275 mV, 300 mV, 325 mV, 350 mV, 375 mV, 400 mV, or more than 400 mV. In some cases, voltage is at most 10 mV, 20 mV, 30 mV, 40 mV, 50 mV, 60 mV, 70 mV, 80 mV, 90 mV, 100 mV, 125 mV, 150 mV, 175 mV, 200 mV, 225 mV, 250 mV, 275 mV, 300 mV, 325 mV, 350 mV, 375 mV, 400 mV, or more than 400 mV.

In some instances, an electrode disclosed herein is a silver/silver chloride (Ag/AgCl) electrode. Non-limiting examples of the electrode is a standard hydrogen electrode (SHE), a saturated calomel electrode (SCE), a copper-copper(II) sulfate electrode, and a metal electrode. The metal electrode may be at least one of a platinum electrode and a silver/silver chloride electrode. In some instances, the electrode is coated such as by polyurethane.

In some instances, the method comprises sequencing a target molecule using a nanopore disclosed herein, wherein the nanopore is in contact with a conductive fluid. In some instances, voltage from the electrical stimulus is adjusted based on a conductive fluid. For example, about 320 mV is used for a salt concentration (e.g., KCl) of approximately 1 M, and can be increased or decreased depending on the salt concentration. In some instances, the conductive fluid comprises an electrolyte. In some instances, the conductive fluid is a salt solution. Exemplary salt solutions include, but are not limited to, KCl, NaCl, $CaCl_2$, and phosphate. Concentration of the salt solution may be at least 25 mM, 50 mM, 100 mM, 125 mM, 150 mM, 175 mM, 200 mM, 225 mM, 250 mM, 275 mM, 300 mM, 325 mM, 350 mM, 375 mM, 400 mM, 450 mM, 500 mM, 550 mM, 600 mM, 650 mM, 700 mM, 750 mM, 800 mM, 850 mM, 900 mM, 950 mM, 1 M, 1.5 M, or 2 M. In some instances, the concentration is in a range of about 25 mM to about 2 M, about 50 mM to about 1.5 M, about 100 mM to about 1 M, about 125 mM to about 950 M, 150 mM to about 900 mM, about 175 mM to about 850 mM, about 200 mM to about 800 mM, about 225 mM to about 750 mM, about 250 mM to about 700 mM, about 275 mM to about 650 mM, about 300 mM to about 600 mM, 325 mM to about 550 mM, 350 mM to about 500 mM, and about 375 mM to about 450 mM. In some instances, the concentration of the salt solution is more than 2 M. In some instances, concentration of salt solution is at most 25 mM, 50 mM, 100 mM, 125 mM, 150 mM, 175 mM, 200 mM, 225 mM, 250 mM, 275 mM, 300 mM, 325 mM, 350 mM, 375 mM, 400 mM, 450 mM, 500 mM, 550 mM, 600 mM, 650 mM, 700 mM, 750 mM, 800 mM, 850 mM, 900 mM, 950 mM, 1 M, 1.5 M, 2 M, or more than 2 M. In some instances, the conductive fluid is not a salt solution. For example, the conductive fluid comprises glycerol or redox molecules.

In some instances, the method comprises sequencing a target molecule using a nanopore disclosed herein, wherein the nanopore is in contact with a conductive fluid of a suitable pH. In some instances, the pH is at least 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 9.2, 9.4, 9.6, 9.8, 10.0, 10.2, 10.4, 10.6, 10.8, 11.0, 11.2, 11.4, 11.6, 11.8, 12.0, 12.2, 12.4, 12.6, 12.8, and 13.0. In some instances, the pH is about 7.4. The pH may be in a range of about 1.0 to about 13.0, about 1.5 to about 12.5, about 2.0 to about 12.0, about 2.5 to about 11.5, about 3 to about 11.0, about 3.0 to about 10.5, about 3.5 to about 10.0, about 4.0 to about 9.5, about 4.5 to about 9, about 5 to about 8.5, about 6.5 to about 8.0, and about 7 to about 7.5.

Methods comprising sequencing a target molecule using a nanopore disclosed herein may be temperature-sensitive. In some instances, the temperature is at least 10° C., 15° C., 20° C., 25° C., 30° C., 35° C., 40° C., 45° C., 50° C., 55° C., 60° C., 65° C., 70° C., or more than 70° C. In some cases, the temperature is room temperature.

In some instances, the method comprises facilitating passage of a target molecule through or in proximity to a nanopore disclosed herein with a molecular motor. The molecular motor may control the rate of translocation of the target molecule across a membrane. In some instances, the molecule motor is an enzyme. Exemplary molecular motors include, but not limited to, RNA polymerase, DNA polymerase, helicases, topoisomerases, proteins that remodel chromatin, proteins that condense chromosomes, and viral nucleic packaging motors.

In some instances, methods disclosed herein comprise sequencing a target molecule once. In some instances, methods disclosed herein comprise sequencing a target molecule only once. For instance, the size of the nanopore may be such that the target molecule is optimally passed through the nanopore (e.g., without bunching or folding of the target molecule), one residue at a time, providing a desirable sequence resolution and accurate sequence reading in a first sequencing reaction. In some instances, methods disclosed herein comprise sequencing a target molecule more than 1 time. In some instances, the target molecule is sequenced at least 1, 2, 3, 4, 5, 6, 7, 8, 9, 10, 12, 14, 16, 18, 20, 25, 30, 35, 40, 45, 50, or more than 50 times. In some cases, the target molecule is sequenced at most 1, 2, 3, 4, 5, 6, 7, 8, 9, 10, 12, 14, 16, 18, 20, 25, 30, 35, 40, 45, 50, or more than 50 times. In some cases, methods and compositions described herein involve parallel sequencing.

The target DNA for sequencing may be a synthetic DNA or a DNA obtained from a biological sample. In some instances, the DNA comprises about 5, 10, 15, 20, 25, 30, 35, 40, 45, 50, 100, 150, 200, 300, 400, 500, 2000, 4000, 6000, 8000, 10000, 20000, 50000, 100000, or more than 100000 nucleotides. DNA that is sequenced can comprise about 100000, 50000, 20000, 10000, 8000, 6000, 4000, 2000, 500, 400, 300, 200, 150, 100, 50, 45, 35, 30, 25, 20, 19, 18, 17, 16, 15, 14, 13, 12, 11, 10, or less than 10 nucleotides. The number of nucleotides sequenced may be in a range of about 1 to about 100000 nucleotides, about 1 to about 10000 nucleotides, about 1 to about 1000 nucleotides, about 1 to about 500 nucleotides, about 1 to about 300 nucleotides, about 1 to about 200 nucleotides, about 1 to about 100 nucleotides, about 5 to about 100000 nucleotides, about 5 to about 10000 nucleotides, about 5 to about 1000 nucleotides, about 5 to about 500 nucleotides, about 5 to about 300 nucleotides, about 5 to about 200 nucleotides, about 5 to about 100 nucleotides, about 10 to about 100000 nucleotides, about 10 to about 10000 nucleotides, about 10 to about 1000 nucleotides, about 10 to about 500 nucleotides, about 10 to about 300 nucleotides, about 10 to about 200 nucleotides, about 10 to about 100 nucleotides, about 20 to about 100000 nucleotides, about 20 to about 10000 nucleotides, about 20 to about 1000 nucleotides, about 20 to about 500 nucleotides, about 20 to about 300 nucleotides, about 20 to about 200 nucleotides, about 20 to about 100 nucleotides, about 30 to about 100000 nucleotides, about 30 to about 10000 nucleotides, about 30 to about 1000 nucleotides, about 30 to about 500 nucleotides, about 30 to about 300 nucleotides, about 30 to about 200 nucleotides, about 30 to about 100 nucleotides, about 50 to about 100000 nucleotides, about 50 to about 10000 nucleotides, about 50 to about 1000 nucleotides, about 50 to about 500 nucleotides, about 50 to about 300 nucleotides, about 50 to about 200 nucleotides, or about 50 to about 100 nucleotides.

In some instances, RNA is sequenced. The target RNA for sequencing may be a synthetic RNA or RNA obtained from a biological sample. In some instances, the RNA comprises about 5, 10, 15, 20, 25, 30, 35, 40, 45, 50, 100, 150, 200, 300, 400, 500, 2000, 4000, 6000, 8000, 10000, 20000, 50000, 100000, or more than 100000 nucleotides. RNA that is sequenced can comprise about 100000, 50000, 20000, 10000, 8000, 6000, 4000, 2000, 500, 400, 300, 200, 150, 100, 50, 45, 35, 30, 25, 20, 19, 18, 17, 16, 15, 14, 13, 12, 11, 10, or less. The number of nucleotides sequenced may be in a range of about 1 to about 100000 nucleotides, about 1 to about 10000 nucleotides, about 1 to about 1000 nucleotides, about 1 to about 500 nucleotides, about 1 to about 300 nucleotides, about 1 to about 200 nucleotides, about 1 to about 100 nucleotides, about 5 to about 100000 nucleotides, about 5 to about 10000 nucleotides, about 5 to about 1000 nucleotides, about 5 to about 500 nucleotides, about 5 to about 300 nucleotides, about 5 to about 200 nucleotides, about 5 to about 100 nucleotides, about 10 to about 100000 nucleotides, about 10 to about 10000 nucleotides, about 10 to about 1000 nucleotides, about 10 to about 500 nucleotides, about 10 to about 300 nucleotides, about 10 to about 200 nucleotides, about 10 to about 100 nucleotides, about 20 to about 100000 nucleotides, about 20 to about 10000 nucleotides, about 20 to about 1000 nucleotides, about 20 to about 500 nucleotides, about 20 to about 300 nucleotides, about 20 to about 200 nucleotides, about 20 to about 100 nucleotides, about 30 to about 100000 nucleotides, about 30 to about 10000 nucleotides, about 30 to about 1000 nucleotides, about 30 to about 500 nucleotides, about 30 to about 300 nucleotides, about 30 to about 200 nucleotides, about 30 to about 100 nucleotides, about 50 to about 100000 nucleotides, about 50 to about 10000 nucleotides, about 50 to about 1000 nucleotides, about 50 to about 500 nucleotides, about 50 to about 300 nucleotides, about 50 to about 200 nucleotides, or about 50 to about 100 nucleotides.

In some instances, a peptide is sequenced. In some instances, a polypeptide is sequenced. Generally, one of skill in the art considers a peptide to be less than about 100 amino acids, and a polypeptide to be greater than about 100 amino acids. In some instances, the peptide is about 5 amino acids to about 100 amino acids in length. In some instances, the polypeptide is about 100 amino acids to about 40,000 amino acids. In some instances, the polypeptide is about 100 amino acids to about 30,000 amino acids. In some instances, the polypeptide is about 100 amino acids to about 20,000 amino acids. In some instances, the polypeptide is about 100 amino acids to about 10,000 amino acids. In some instances, the polypeptide is about 100 amino acids to about 8,000 amino acids. In some instances, the polypeptide is about 100 amino acids to about 6,000 amino acids. In some instances, the polypeptide is about 100 amino acids to about 4,000 amino acids. In some instances, the polypeptide is about 100 amino acids to about 2,000 amino acids. In some instances, the polypeptide is about 100 amino acids to about 1,000 amino acids.

A nucleotide as sequenced using systems and methods described herein can be a primary nucleotide or a nucleotide analog. For example, a primary nucleotide is deoxyadenosine mono-phosphate (cAMP), deoxycytidine mono-phosphate (dCMP), deoxyguanosine mono-phosphate (dGMP) or deoxythymidine mono-phosphate (dTMP). A nucleotide analog can be an analog or mimic of a primary nucleotide having modification on the primary nucleobase (A, C, G and T), the deoxyribose structure, the phosphate group of the primary nucleotide, or any combination thereof. Examples of modified bases include, but not limited to, methylated nucleobases, modified purine bases (e.g. hypoxanthine, xanthine, 7-methylguanine, isodG), modified pyrimidine bases (e.g. 5,6-dihydrouracil and 5-methylcytosine, isodC), universal bases (e.g. 3-nitropyrrole and 5-nitroindole), non-binding base mimics (e.g. 4-methylbezimidazole and 2,4-diflurotoluene or benzene), and no base (abasic nucleotide where the nucleotide analog does not have a base). Examples of nucleotide analogs having modified deoxyribose (e.g. dideoxynucleosides such as dideoxyguanosine, dideoxyadenosine, dideoxythymidine, and dideoxycytidine) and/or phosphate structure include, but not limited to, glycol nucleotides, morpholinos, and locked nucleotides.

Sequencing using nanopores described herein can result in a low error rate. In some instances, the error rate is about 20%, 10%, 5%, 4%, 3%, 2%, 1%, 0.5%, 0.1%, or less than 0.1%. In some instances, the error rate is at most 20%, 10%, 5%, 4%, 3%, 2%, 1%, 0.5%, 0.1%, or less than 0.1%. Sequencing using nanopores described herein can result in high accuracy. For example, the accuracy is at least 75%, 80%, 85%, 90%, 95%, 97%, 98%, or 99%. In some instances, the accuracy is about 75%, 80%, 85%, 90%, 95%, 97%, 98%, or 99%.

In some instances, a target molecule that is sequenced further comprises a label. The label can be chemically or biologically reactive. Exemplary labels include, but not limited to, a ligand, a polymer, a vitamin, a fluorescent molecule, a bead, or a probe.

Provided herein are methods and systems for sequencing a target molecule in a suitable amount of time comprising contacting a nanopore disclosed herein with the target molecule. At least one subunit of a target molecule to be detected (e.g., nucleotide residue or amino acid) can be detected within any suitable amount of time. In some instances, the at least one subunit of the target molecule is detected in a time period of about 1 second, 1 millisecond (ms), 1 microsecond, or less than 1 microsecond. In some instances, the at least one subunit of the target molecule is detected in a time period of at most 1 second, 1 millisecond (ms), 1 microsecond, or less than 1 microsecond. In some instances, the at least one subunit of the target molecule is detected in a time period of at least 1 second, 1 millisecond (ms), 1 microsecond, or less than 1 microsecond.

Provided herein are methods and systems for generating a sequence of a target molecule comprising contacting a nanopore disclosed herein with the target molecule in a desirable time frame. In some instances, the methods comprise generating a sequence of as many as 3 billion subunits in less than about 1 hour. In some instances, the methods comprise generating a sequence of as many as 1 million subunits in less than about 5 minutes. In some instances, the methods comprise generating a sequence of as many as 1000 subunits in less than about 1 minute.

Computer Systems

Described herein, in certain embodiments, are methods and systems for use with a reaction device. The reaction device may comprise a sensor that has an electrical circuit adjacent to a membrane comprising a nanopore. In some instances, the electrical circuit generates an electrical signal in response to detection of a target molecule upon passage through or in proximity of the nanopore. In some instances, the reaction device supports a plurality of nanopores. The reaction device may contain or be capable of containing reagents for a sequencing reaction with a nanopore disclosed herein. The reaction device may comprise a reservoir. In some instances, the reservoir is capable of containing or receiving material (e.g., a target molecule) for analysis. In some instances, the device comprises an additional reservoir. The additional reservoir may be used for waste.

In some instances, the device is portable. In some instances, the device is hand-held and/or capable of being carried by hand. The device may be at most 150 grams (g). In some instances, the device is at most 1000 g, 750 g, 500 g, 450 g, 425 g, 400 g, 375 g, 350 g, 325 g, 300 g, 275 g, 250 g, 225 g, 200 g, 175 g, 150 g, 125 g, 100 g, 90 g, 85 g, 80 g, 75 g, 70 g, 65 g, 60 g, 55 g, 50 g, 45 g, 40 g, 35 g, 30 g, 25 g, 20 g, or less than 20 g. The device may have a volume of 80000 $mm^3$. In some cases, the device has a volume of at most 500000 $mm^3$, 400000 $mm^3$, 300000 $mm^3$, 200000 $mm^3$, 100000 $mm^3$, 50000 $mm^3$, 20000 $mm^3$, 10000 $mm^3$, 8000 $mm^3$, 6000 $mm^3$, 4000 $mm^3$, 2000 $mm^3$, 500 $mm^3$, 400 $mm^3$, 300 $mm^3$, 200 $mm^3$, 150 $mm^3$, 100 $mm^3$, 50 $mm^3$, 45 $mm^3$, 35 $mm^3$, 30 $mm^3$, 25 $mm^3$, 20 $mm^3$, 10 $mm^3$, or less than 10 $mm^3$.

In some instances the reaction device is connected to a computer system or a computer network. In some instances the reaction device is capable of connecting to a computer system or a computer network. The device may have a computer connecting feature (e.g., USB connector). The device may have a computer connecting wire or cable (e.g., a firewire). The device may have a computer interfacing device. The computer interfacing device may be a device capable of communicating with a computer system or computer network. The computer interfacing device may comprise wireless technology. Non-limiting examples of a computer interfacing device is a Bluetooth chip.

Described herein, in certain embodiments, are methods and systems for sequencing comprising use of a computer network. In some instances, systems described herein comprise a nanopore disclosed herein and a computer system or computer network. In some instances, systems described herein comprise a nanopore disclosed herein, a reaction device disclosed herein, and a computer system or computer network. In some instances, methods disclosed herein comprise connecting a reaction device to a computer system or computer network. In some instances, signal detected upon passage of a target molecule in or through a nanopore is collected using a computer network. In some instances, the computer network comprises one or more computers operably connected to one or more data storage systems. The data storage systems retain an archive of all samples acquired at a local site, wherein operably connected may be wireless or physical. In some instances, the computer network comprises a plurality of computers and/or devices which are connected by physical or wireless means. A computer of the network may be located remotely from the acquisition device. In some instances, the computer network comprises one or more acquisition computers for controlling the acquisition of a sequencing sample. In some instances, the network comprises at least one display for viewing the acquired data. In some instances, the at least one display is a component of a viewing terminal of the network. A viewing terminal may be located remotely from the acquisition device. A computer, in various implementations, comprises software. In some cases, the computer network comprises the internet. In some cases, the computer network comprises a web browser.

In some instances, methods and compositions as disclosed herein involve at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular data types. In some instances, a computer program includes a standalone application, which is a program that is run as an independent computer process, not an add-on to an existing process, e.g., not a plug-in.

In some cases, a computer comprises external devices. In some instances, communication between a computer and an external device occurs through at least one of physical cable, a storage device, a memory device, and a wireless connection. In some cases, a system interfaces with software system on a personal computer, tablet, or mobile device A system can include a storage and/or memory device. The storage and/or memory device is one or more physical apparatuses used to store data or programs on a temporary or permanent basis. In some cases, the device is volatile memory and requires power to maintain stored information. Alternately or in combination, a device is non-volatile memory and retains stored information when the digital processing device is not powered. For example, non-volatile memory comprises at least one of flash memory, dynamic random-access memory (DRAM), ferroelectric random access memory (FRAM), phase-change random access memory (PRAM). In some cases, a device is a storage device including, by way of non-limiting examples, CD-ROMs, DVDs, flash memory devices, magnetic disk drives, magnetic tapes drives, optical disk drives, and cloud computing based storage. In some instances, the storage and/or memory device is a combination of devices such as those disclosed herein. Alternately or in combination, data could be stored in a database that can be accessed at a later point or analyzed by third-party applications.

Applications

Described herein, in certain embodiments, are methods and compositions for detecting a target molecule (e.g., RNA, DNA, or peptide) comprising contacting nanopores disclosed herein with the target molecule. Further described herein, in certain embodiments, are methods and compositions for quantifying a target molecule comprising contacting nanopores disclosed herein with the target molecule. In some instances, the target molecule is from a cell. Non-limiting examples of cells include mammalian cells, human cells, non-human mammalian cells, eukaryotic cells, prokaryotic cells, animal cells, insect cells, bacteria cells, microbial cells, fungal cells, amphibian cells, and fish cells. The cells can originate from a variety of tissues including but not limited to: neural crest tissue, endodermal tissue, ectodermal tissue, mesodermal tissue, and mesenchymal tissue. Cell types may include, but are not limited to, breast cells, brain cells, neural cells, pancreatic cells, liver cells, gall bladder cells, gastrointestinal cells, stomach cells, kidney cells, cells of the reproductive system, heart cells, skin cells, colon cells, urethral cells, endodermal cells, muscle cells, fibroblasts, adipocytes, tumor cells, cancer cells, virally-infected cells, bacterial infected cells, stem cells, dividing cells, apoptotic cells, necrotic cells, blood cells, white blood cells, and stromal cells. In some instances, a target molecule is detected that is isolated from bodily fluids of a subject (e.g., blood, urine, serum, lymph, saliva, and/or perspiration). In some instances, the target molecule is isolated from a subject who has a disease. In some instances, the target molecule is from a virus, bacteria, fungus, or parasite.

In some instances, methods and compositions as described herein are used for at least one of detecting an infectious organism, detecting a disease, diagnosing a disease, detecting disease onset or recurrence, detecting subject response to treatment versus population bases, and monitoring of therapy in a subject. In some instances, methods and compositions as described herein are used for drug development screening. In some instances, methods and compositions as described herein are used for phylogenetic classification. In some instances, methods and compositions as described herein are used for parental and forensic identification. In some instances, sequencing using methods and compositions as described herein is used to detect a nucleic acid mutation that is associated with a disease. For example, several mutations have been identified by genome wide association studies to be associated with cancer. Exemplary types of cancers include, but not limited to, bladder cancer, lung cancer, brain cancer, melanoma, breast cancer, non-Hodgkin lymphoma, cervical cancer, ovarian cancer, colorectal cancer, pancreatic cancer, esophageal cancer, prostate cancer, kidney cancer, skin cancer, leukemia, thyroid cancer, liver cancer, or uterine cancer.

Methods and compositions relating to synthesized nanopores as described herein can be used with a point of care system. For example, disease diagnosis, monitoring of a therapy, detection of a target molecule in a subject using synthesized nanopores can be performed at or near a location of patient care. In some instances, the point of care system is configured to provide monitoring at predetermined intervals or in real-time. In some cases, the intervals are calculated, regulated, or set by a user. Users can include, but not limited to, a subject under treatment or a healthcare provider (e.g., doctor, nurse, technician). In some instances, the intervals are calculated or otherwise determined by the system, such as with the aid of the POC system that determines when a measurement is required.

Without further elaboration, it is believed that one skilled in the art, using the preceding description, can utilize the present invention to the fullest extent. The following examples are illustrative only, and not limiting of the remainder of the disclosure in any way whatsoever.

NUMBERED EMBODIMENTS

The disclosure is further elucidated by reference to the numbered embodiments herein. Numbered embodiment 1 comprises a method of detecting a target molecule, the method comprising: (a) contacting the target molecule with a membrane comprising a macrocycle nanopore, wherein the nanopore has a non-collapsible cavity; and (b) measuring an electrical stimulus across the membrane, wherein transport of the target molecule causes a change in the electrical stimulus. Numbered embodiment 2 comprises the method of numbered embodiment 1, wherein the nanopore is formed by aromatic compounds. Numbered embodiment 3 comprises the method of numbered embodiments 1-2, wherein the nanopore is formed by oligohydrazides. Numbered embodiment 4 comprises the method of numbered embodiments 1-3, wherein 2 or more nanopores are stacked together to form a nanotube. Numbered embodiment 5 comprises the method of numbered embodiments 1-4, wherein formation of the nanotube is dependent on at least one of temperature, solvent, and concentration. Numbered embodiment 6 comprises the method of numbered embodiments 1-5, wherein a diameter of a cavity of the nanopore is in a range of about 0.5 nm to about 3 nm. Numbered embodiment 7 comprises the method of numbered embodiments 1-6, wherein a diameter of a cavity of the nanopore is about 2 nm. Numbered embodiment 8 comprises the method of numbered embodiments 1-7, wherein the membrane is a lipid bilayer. Numbered embodiment 9 comprises the method of numbered embodiments 1-8, wherein the lipid bilayer is from a cell. Numbered embodiment 10 comprises the method of numbered embodiments 1-9, wherein the cell is a red blood cell. Numbered embodiment 11 comprises the method of numbered embodiments 1-10, wherein the electrical stimulus is at least one of applied current and an applied voltage. Numbered embodiment 12 comprises the method of numbered embodiments 1-11, wherein the target molecule is at least one of RNA, DNA, and a peptide. Numbered embodiment 13 comprises the method of numbered embodiments 1-12, wherein the transport of the target molecule is through the cavity. Numbered embodiment 14 comprises the method of numbered embodiments 1-13, wherein the transport of the target molecule is in proximity to the nanopore. Numbered embodiment 15 comprises the method of numbered embodiments 1-14, wherein the transport of a subunit of the target molecule is measured. Numbered embodiment 16 comprises the method of numbered embodiments 1-15, wherein the subunit of the target molecule is a nucleotide. Numbered embodiment 17 comprises the method of numbered embodiments 1-16, further comprising the step of generating a sequence of the target molecule. Numbered embodiment 18 comprises the method of numbered embodiments 1-17, wherein the nanopore comprises at least one compound of Formula I:

wherein:
$R^1$ is —$CH_2CH_2CH_2CH_3$; and
$R^2$ is —$CH_2CH_2$=$CH_3$ or —$(CH_2)_3S(CH_2)_4O(CH_2)_4O(CH_2)_4OH$.

Numbered embodiment 19 comprises the method of synthesizing a nanopore for use in detecting a target molecule, the method comprising:

(a) providing a reactant of Formula II;

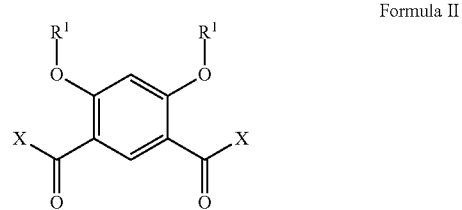

Formula II (b) providing a reactant of Formula III; and

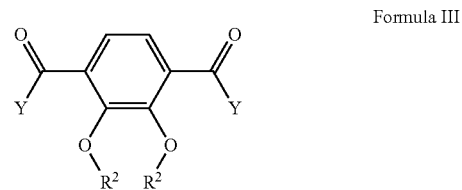

Formula III

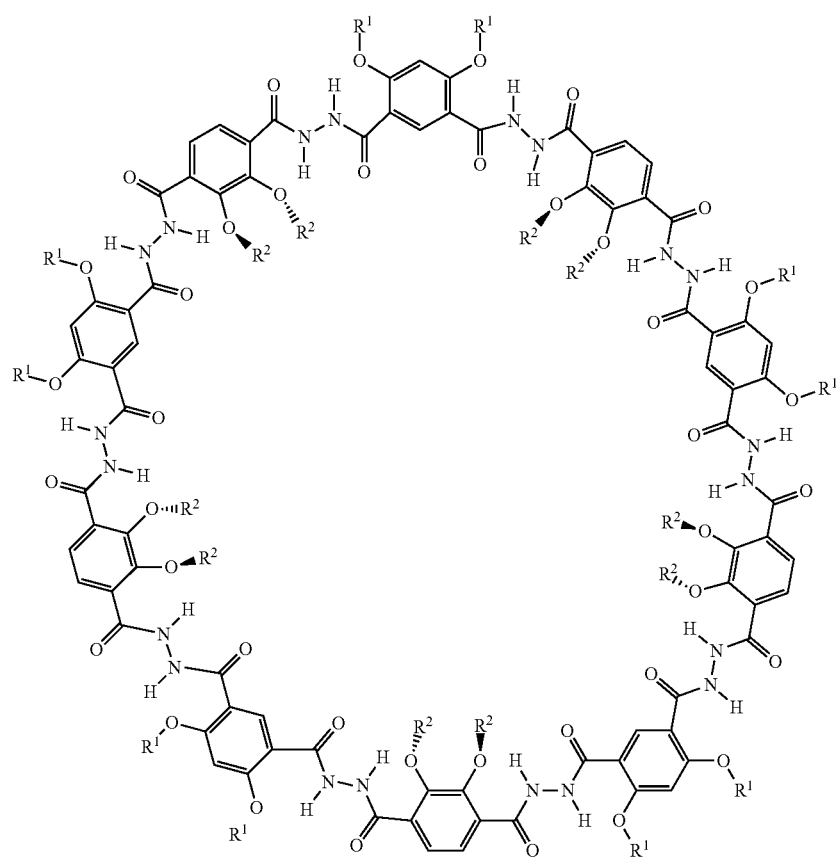

Formula I (c) combining the reactant of Formula II and the reactant of Formula III to yield a product of Formula I,

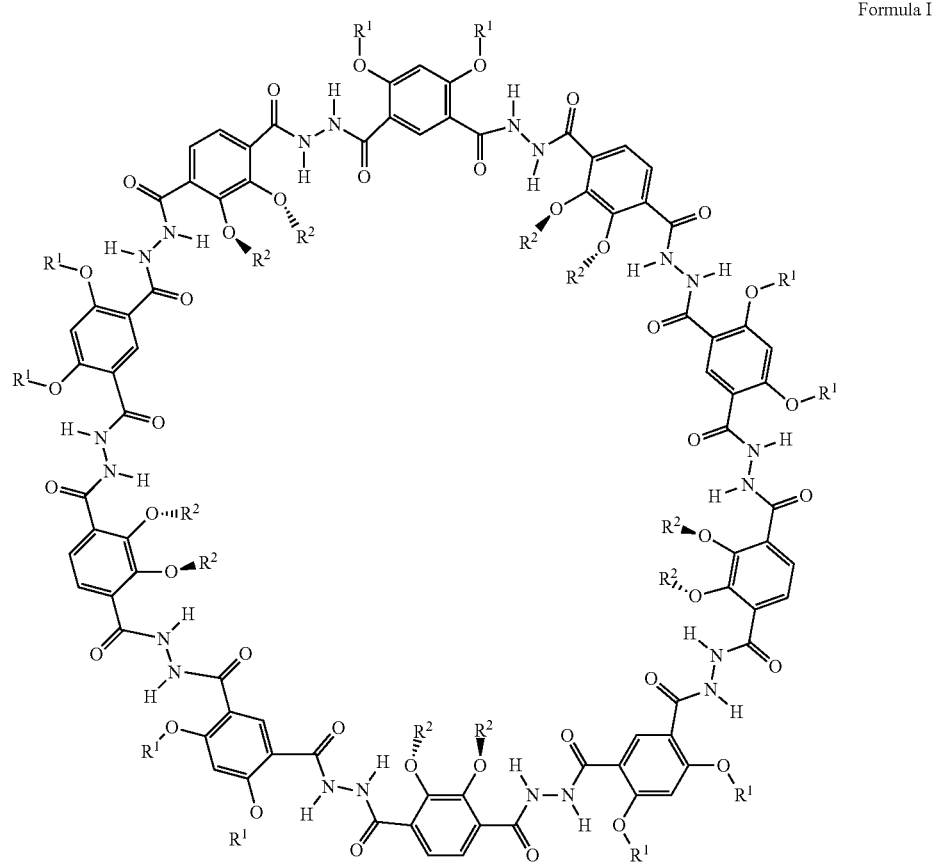

Formula I wherein:
R$^1$ is —CH$_2$CH$_2$CH$_2$CH$_3$;
X is Cl;
R$^2$ is —CH$_2$CH$_2$=CH$_3$ or —(CH$_2$)$_3$S(CH$_2$)$_4$O(CH$_2$)$_4$O(CH$_2$)$_4$OH;
Y is NHNH$_2$; and wherein the product of Formula I is used for detecting a target molecule.

Numbered embodiment 20 comprises the method of numbered embodiments 1-19, wherein 2 or more nanopores are stacked together to form a nanotube. Numbered embodiment 21 comprises the method of numbered embodiments 1-20, wherein formation of the nanotube is dependent on at least one of temperature, solvent, and concentration. Numbered embodiment 22 comprises the method of numbered embodiments 1-21, wherein a diameter of a cavity of the nanopore is in a range of about 0.5 nm to about 3 nm. Numbered embodiment 23 comprises the method of numbered embodiments 1-22, wherein a diameter of a cavity of the nanopore is about 2 nm. Numbered embodiment 24 comprises the method of numbered embodiments 1-23, wherein the nanopore assembles in a membrane. Numbered embodiment 25 comprises the method of numbered embodiments 1-24, wherein the membrane is a lipid bilayer. Numbered embodiment 26 comprises the method of numbered embodiments 1-25, wherein the lipid bilayer is from a cell. Numbered embodiment 27 comprises the method of numbered embodiments 1-26, wherein the cell is a red blood cell. Numbered embodiment 28 comprises the method of numbered embodiments 1-27, the target molecule is detected by applying an electrical stimulus. Numbered embodiment 29 comprises the method of numbered embodiments 1-28, wherein the electrical stimulus is at least one of applied current and an applied voltage. Numbered embodiment 30 comprises the method of numbered embodiments 1-29, wherein the target molecule is at least one of RNA, DNA, and a peptide. Numbered embodiment 31 comprises the method of numbered embodiments 1-30, wherein a transport of the target molecule is through a cavity. Numbered embodiment 32 comprises the method of numbered embodiments 1-31, wherein a transport of the target molecule is in proximity to the nanopore. Numbered embodiment 33 comprises the method of numbered embodiments 1-32, wherein a subunit of the target molecule is detected. Numbered embodiment 34 comprises the method of numbered embodiments 1-33, wherein the subunit of the target molecule is a nucleotide. Numbered embodiment 35 comprises the method of numbered embodiments 1-34, further comprising a step of generating a sequence of the target molecule. Numbered embodiment 36 comprises the method of numbered embodiments 1-35, wherein the nanopore comprises a cavity that is non-collapsible. Numbered embodiment 37 comprises a method of at least one of drug development screening, disease diagnosis, phylogenetic classification, parental and forensic identification, disease onset and recurrence, individual response to treatment versus population bases, and monitoring of therapy using any of the methods of the preceding claims. Numbered embodiment 38 comprises a method of sequencing the target molecule at point of care using any one of the preceding claims. Numbered embodiment 39 comprises a composition comprising a nanopore of Formula I, wherein Formula I is Numbered embodiment 40 comprises the composition of numbered embodiments 1-39, wherein 2 or more nanopores are stacked together to form a nanotube. Numbered embodiment 41 comprises the composition of numbered embodiments 1-40, wherein formation of the nanotube is dependent on at least one of temperature, solvent, and concentration. Numbered embodiment 42 comprises the composition of numbered embodiments 1-41, wherein a diameter of a cavity of the nanopore is in a range of about 0.5 nm to about 3 nm. Numbered embodiment 43 comprises the composition of numbered embodiments 1-42, wherein a diameter of a cavity of the nanopore is about 2 nm. Numbered embodiment 44 comprises the composition of numbered embodiments 1-43, wherein the membrane is a lipid bilayer. Numbered embodiment 45 comprises the composition of numbered embodiments 1-44, wherein the lipid bilayer is from a cell. Numbered embodiment 46 comprises the composition of numbered embodiments 1-45, wherein the cell is a red blood cell. Numbered embodiment 47 comprises a composition comprising a nanopore of Formula I, wherein Formula I is

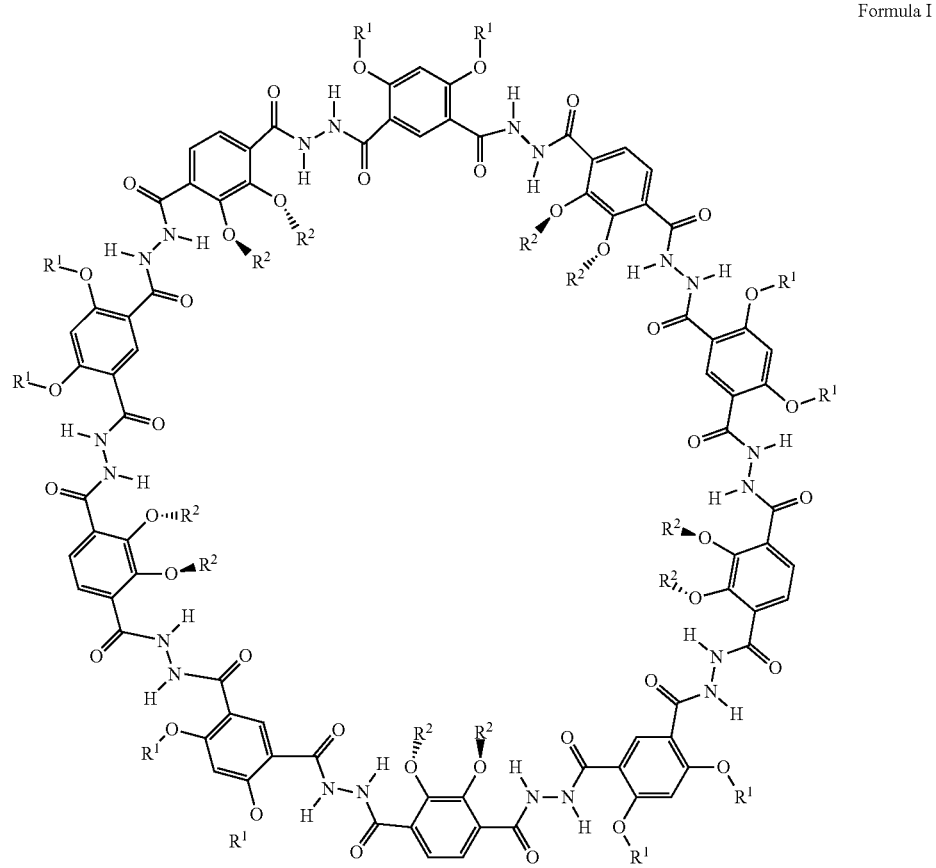

Formula I wherein:
$R^1$ is —$CH_2CH_2CH_2CH_3$;
$R^2$ is —$CH_2CH_2=CH_3$ or —$(CH_2)_3S(CH_2)_4O(CH_2)_4O(CH_2)_4OH$;
and a membrane.

Formula I

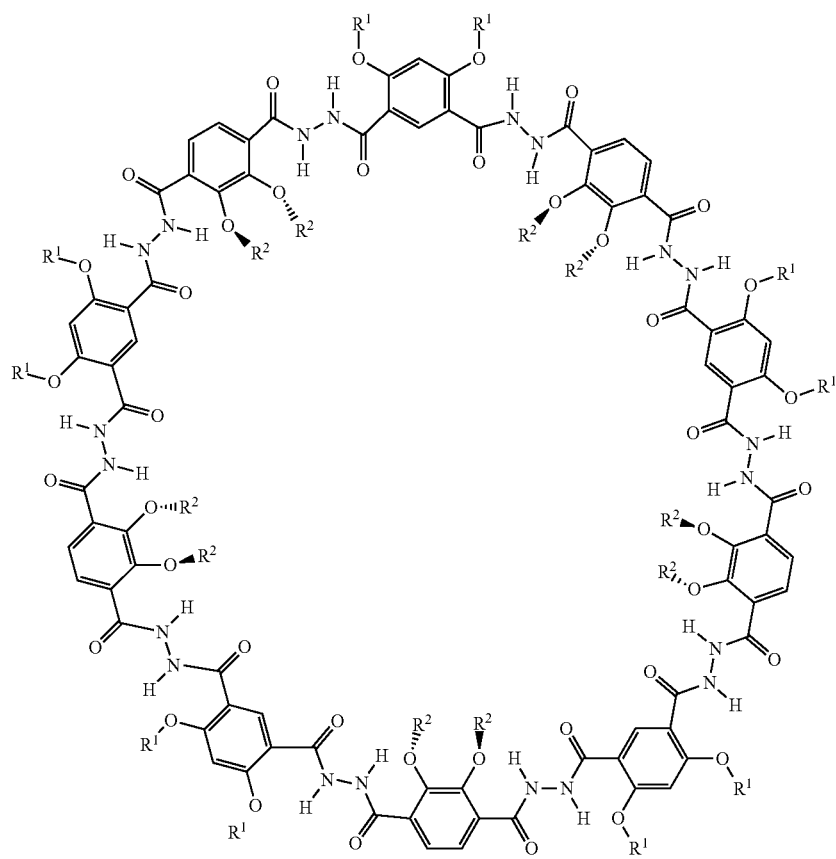

wherein:
R¹ is —CH₂CH₂CH₂CH₃;
R² is —CH₂CH₂=CH₃ or —(CH₂)₃S(CH₂)₄O(CH₂)₄O(CH₂)₄OH.

Numbered embodiment 48 comprises the composition of numbered embodiments 1-47, wherein 2 or more nanopores are stacked together to form a nanotube. Numbered embodiment 49 comprises the composition of numbered embodiments 1-48, wherein formation of the nanotube is dependent on at least one of temperature, solvent, and concentration. Numbered embodiment 50 comprises the composition of numbered embodiments 1-49, wherein a diameter of a cavity of the nanopore is in a range of about 0.5 nm to about 3 nm. Numbered embodiment 51 comprises the composition of numbered embodiments 1-50, wherein a diameter of a cavity of the nanopore is about 2 nm. Numbered embodiment 52 comprises a method of detecting a target molecule, the method comprising: (a) contacting the target molecule with a membrane comprising the nanopore of numbered embodiments 1-51, wherein the nanopore has a non-collapsible cavity; and (b) measuring an electrical stimulus across the membrane, wherein transport of the target molecule causes a change in the electrical stimulus. Numbered embodiment 53 comprises the method of numbered embodiments 1-52, wherein the membrane is a lipid bilayer. Numbered embodiment 54 comprises the method of numbered embodiments 1-53, wherein the lipid bilayer is from a cell. Numbered embodiment 55 comprises the method of numbered embodiments 1-54, wherein the cell is a red blood cell. Numbered embodiment 56 comprises the method of numbered embodiments 1-55, wherein the electrical stimulus is at least one of applied current and an applied voltage. Numbered embodiment 57 comprises the method of numbered embodiments 1-56, wherein the target molecule is at least one of RNA, DNA, and a peptide. Numbered embodiment 58 comprises the method of numbered embodiments 1-57, wherein the transport of the target molecule is through the cavity. Numbered embodiment 59 comprises the method of numbered embodiments 1-58, wherein the transport of the target molecule is in proximity to the nanopore. Numbered embodiment 60 comprises the method of numbered embodiments 1-59, wherein the transport of a subunit of the target molecule is measured. Numbered embodiment 61 comprises the method of numbered embodiments 1-60, wherein the subunit of the target molecule is a nucleotide. Numbered embodiment 62 comprises the method of numbered embodiments 1-61, further comprising the step of generating a sequence of the target molecule. Numbered embodiment 63 comprises a method for making a nanopore for use in detecting a target molecule, the method comprising:

(a) providing a reactant of Formula II;

Formula II

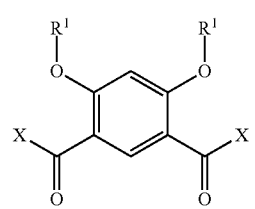

(b) providing a reactant of Formula III; and

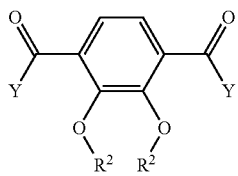

Formula III (c) combining the reactant of Formula II and the reactant of Formula III to yield a product comprising the composition of numbered embodiments 1-62.

Numbered embodiment 64 comprises the method of numbered embodiments 1-63, wherein the nanopore assembles in a membrane. Numbered embodiment 65 comprises the method of numbered embodiments 1-64, wherein the membrane is a lipid bilayer. Numbered embodiment 66 comprises the method of numbered embodiments 1-65, wherein the lipid bilayer is from a cell. Numbered embodiment 67 comprises the method of numbered embodiments 1-66, wherein the cell is a red blood cell. Numbered embodiment 68 comprises the method of numbered embodiments 1-67, wherein the target molecule is detected by applying an electrical stimulus. Numbered embodiment 69 comprises the method of numbered embodiments 1-68, wherein the electrical stimulus is at least one of applied current and an applied voltage. Numbered embodiment 70 comprises the method of numbered embodiments 1-69, wherein the target molecule is at least one of RNA, DNA, and a peptide. Numbered embodiment 71 comprises the method of numbered embodiments 1-70, wherein a transport of the target molecule is through a cavity. Numbered embodiment 72 comprises the method of numbered embodiments 1-71, wherein a transport of the target molecule is in proximity to the nanopore. Numbered embodiment 73 comprises the method of numbered embodiments 1-72, wherein a subunit of the target molecule is detected. Numbered embodiment 74 comprises the method of numbered embodiments 1-73, wherein the subunit of the target molecule is a nucleotide. Numbered embodiment 75 comprises the method of numbered embodiments 1-74, further comprising a step of generating a sequence of the target molecule. Numbered embodiment 76 comprises the method of numbered embodiments 1-75, wherein the nanopore comprises a cavity that is non-collapsible. Numbered embodiment 77 comprises a method of at least one of drug development screening, disease diagnosis, phylogenetic classification, parental and forensic identification, disease onset and recurrence, individual response to treatment versus population bases, and monitoring of therapy using any of the methods of the preceding claims. Numbered embodiment 78 comprises a method of sequencing the target molecule at point of care using any one of the preceding claims.

EXAMPLES

The examples and embodiments described herein are for illustrative purposes only and are not intended to limit the scope of the claims provided herein. Various modifications or changes suggested to persons skilled in the art are to be included within the spirit and purview of this application and scope of the appended claims.

Example 1. Synthesis of Nanopores

A nanopore ring was designed and synthesized as seen below.

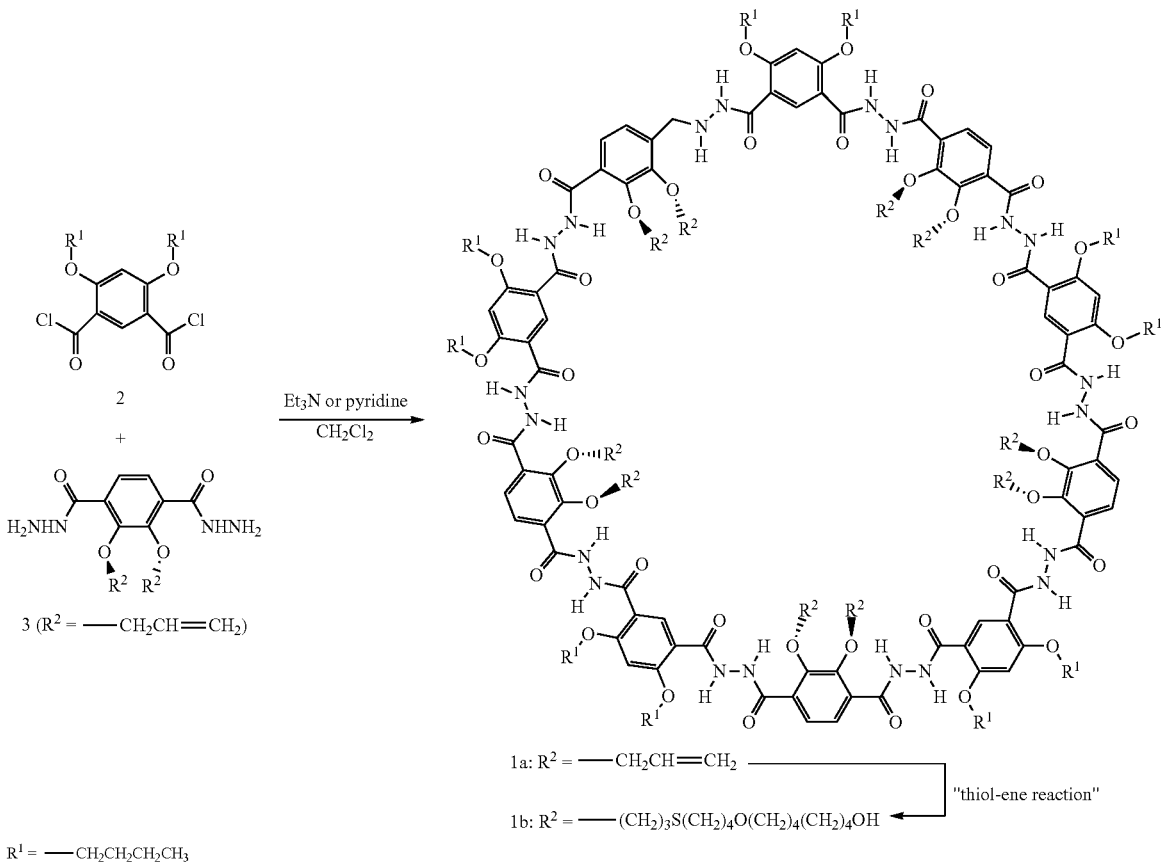

A solution of diacid chloride (2.44 mmol) in methylene chloride (4 mL) was added dropwise to a solution of dihydrazide (2.44 mmol) in methylene chloride (80 mL) at room temperature for one hour in the presence of DIPEA (12.2 mmol). The reaction mixture was heated under reflux for 18 hours, at which point methanol (50 mL) was added. Solvent was evaporated off to yield a solid residue that was then redissolved into methylene chloride. The organic solution was washed with 10% HCl and brine. The solution was dried over sodium sulfate and the solvent was evaporated under vacuum. The resulting solid was recrystallized in methanol to obtain the crude product (1.24 g, 72%).

The crude product was analyzed via MALDI-MS and confirmed to contain the cyclic ring (FIG. 1) as the dominant product. The final product was further derived based on a "thiol-ene" reaction. The crude solid was purified using column chromatography (silica gel in chloroform/methanol, 10:1) to yield cyclic 10 mer (FIG. 1).

Example 2. Another Approach to Synthesis of Nanopores

Nanopores were synthesized using the steps described.

Acyl chloride 4 was synthesized following the reaction steps below. A solution of 2 g of 1 and concentrated 3 ml $H_2SO_4$ in 40 mL of Anhydrous MeOH was heated under reflux for 4-5 hours. The product was obtained upon cooling and was filtered off and washed with a small amount of MeOH, to give pure 1.8 g of 2. A mixture of 1.13 g of 2, 4.15 g $K_2CO_3$, and 4.11 g 1-Bromobutane in 50 mL of Anhydrous DMF was heated at 120° C. for 6 hours. The solid was filtered off, and the solvent was removed in vacuo at 130° C. The residue was dissolved in 100 mL ethyl acetate, and the solution was washed with diluted HCl and with Brine, dried ($MgSO_4$), filtered and evaporated. Evaporation of the solvent gave pure 1.56 g of 3. 1.56 g of 3 was dissolved in THF (30 mL) and a 4% KOH solution (30 mL) was added. This was stirred at room temperature for 1 hour. Water (50 mL) was added and the mixture was washed twice with ether (2×30 mL). The aqueous layer was acidified to around pH 1 with concentrated HCl to precipitate a white solid. After filtration the solid was dried under vacuum with heat, gave pure 1.3 g of product A. 1.3 g A in DCM (25 mL) was treated with 5 ml oxalyl chloride and 1 drop of DMF with stirring over 3 hour. The reaction mixture was concentrated in vacuo, dissolved in DCM (25 mL, Solution A). Solution A is the DCM solution of 4 used in subsequent reactions.

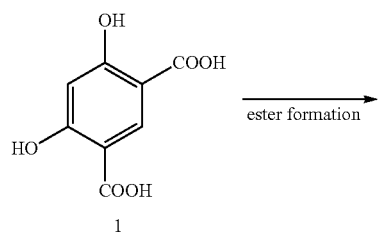

1

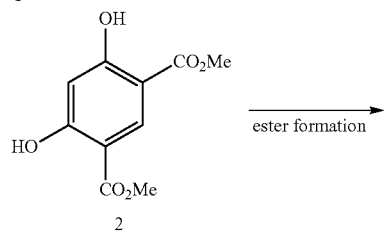

2

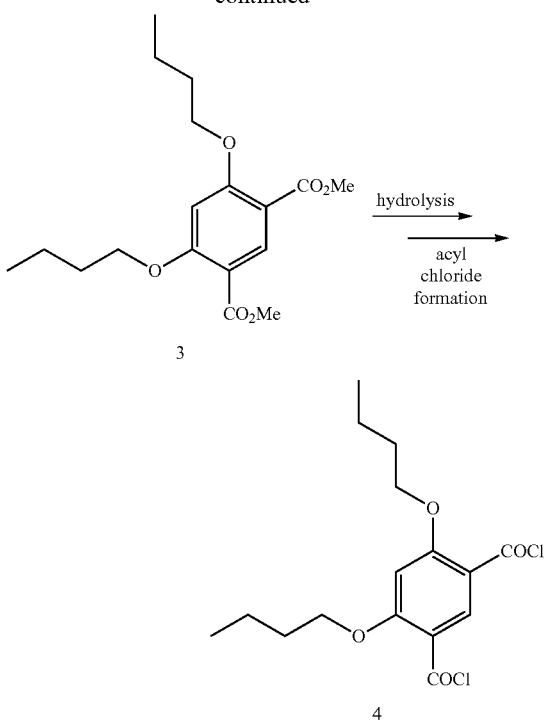

3

4

Hydrazide 8 was synthesized following the reaction steps below. A solution of 1 g 2,3-dihydroxyterephthalic acid (5) and 3.49 g $K_2CO_3$ in acetonitrile (20 mL) was heated at 80° C. for 1 hour. The reaction mixture was then cooled to room temperature and a solution of 2.6 g allyl bromide in acetonitrile (10 mL) was added dropwise. The resulting mixture was heated 17 hours at 70° C. and filtered. The filtrate was evaporated to dryness and diluted in EtOH (100 mL). After adding a solution of NaOH in 20 mL water, the reaction mixture was refluxed for 23 hours and evaporated to dryness. The obtained residue was dissolved in $CH_2Cl_2$ (100 mL) and 150 mL of HCl 1 N were added. The aqueous phase was extracted two times by using $CH_2Cl_2$ (200 mL) and the organic phases put together, washed twice with water (200 mL), dried (MgSO4), filtered and evaporated. After recrystallization in a mixture Et2O/MeOH (50 mL/50 mL), gave pure 1.2 g of 6 as a white powder. To 2.0 g of diethyl ester of terephthalic acid 6 in 20 mL of ethanol was added hydrazine hydrate (2) (98 percent, 2 mL) in ethanol. The solution was refluxed for 3-4 hours. The reaction mixture was allowed to cool to the room temperature and then poured onto ice cold water. The terephthalohydrazide 8 thus obtained, was filtered and recrystallized from ethanol.

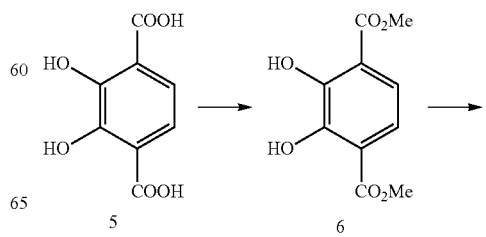

5 6

Following synthesis of hydrazide 8 and side-chain 13, a hydrazide with side-chain 14 was synthesized following the reaction steps below.

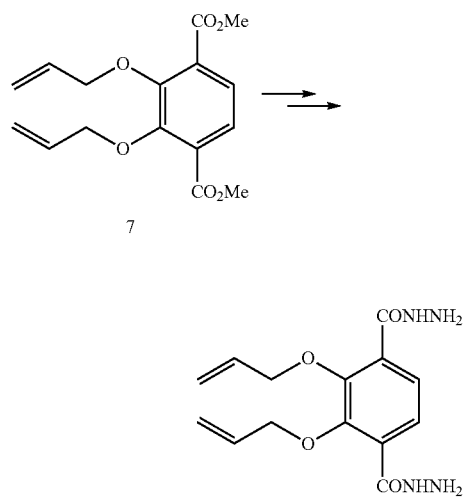

Side-chain 13 was synthesized following the reaction steps below.

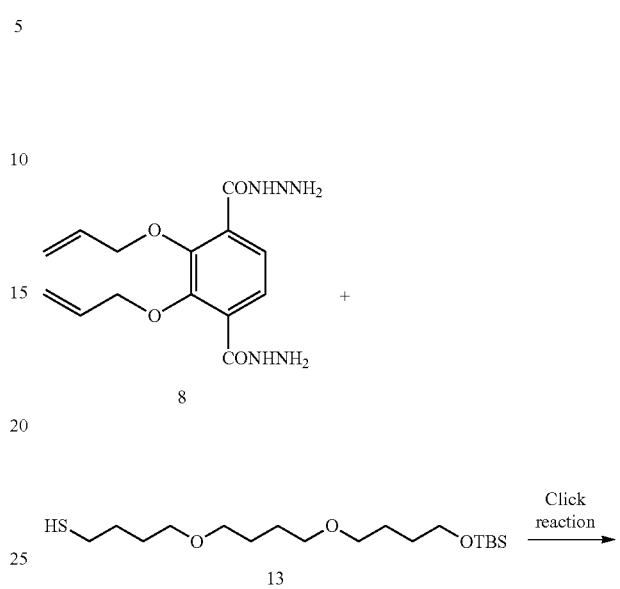

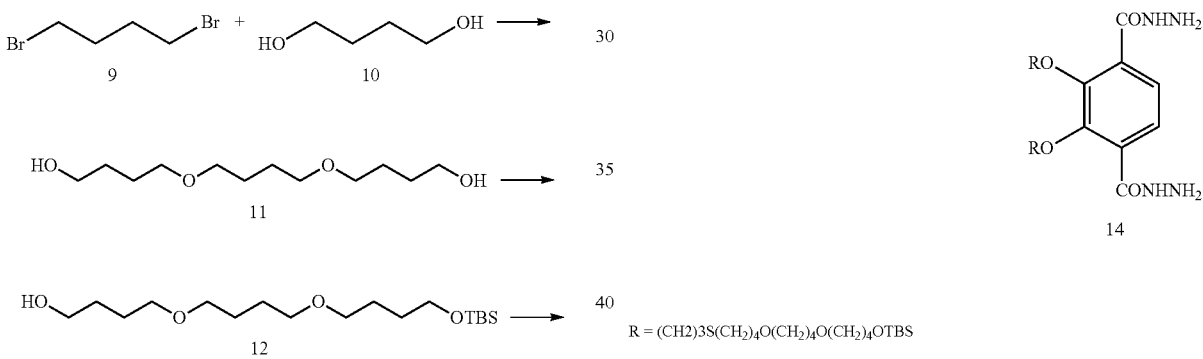

R = (CH2)3S(CH2)4O(CH2)4O(CH2)4OTBS

Macro-cyclization reaction was carried out with a hydrazide with side-chain 14 and acyl chloride 4. The reaction is seen below. The product of the reaction is used as the final nanopore.

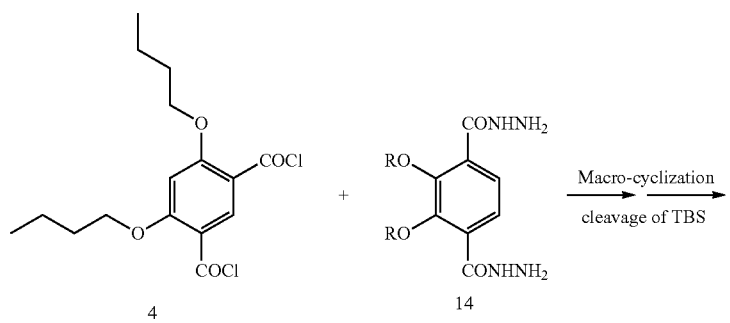

-continued

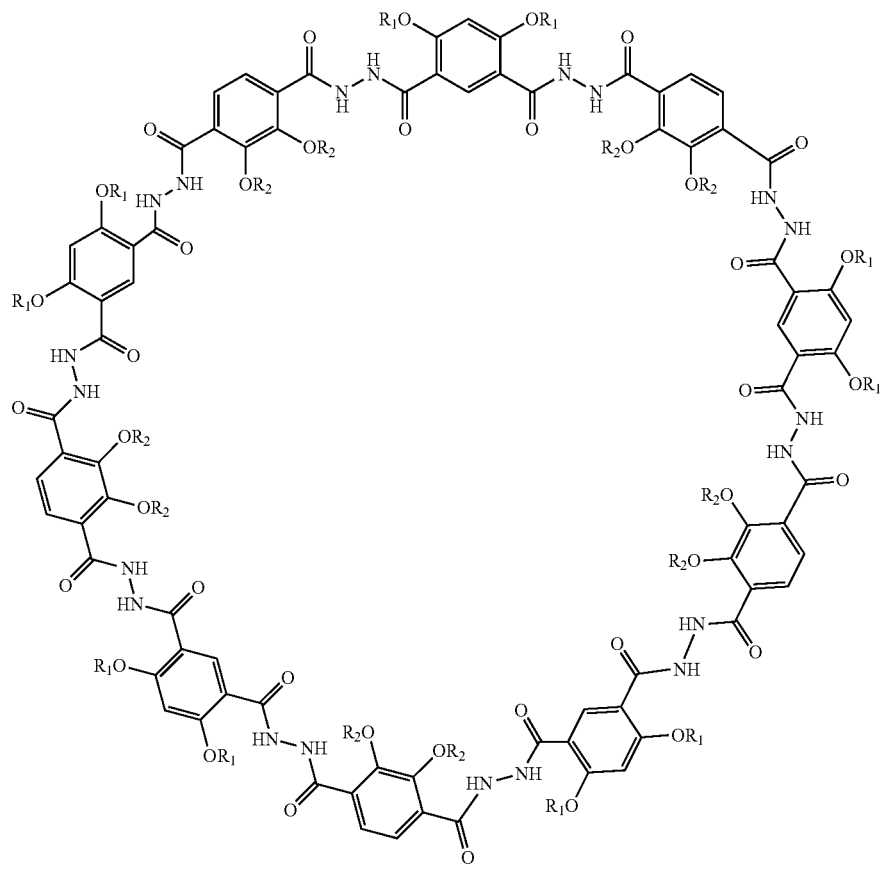

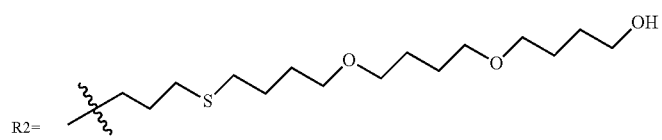

Example 3: Synthesis of Nanopore Using Click Reaction

Nanopores were synthesized using a click reaction.

A solution of 4, 278 mg (0.80 mmol) in CH$_2$Cl$_2$ (5 mL) was added dropwise to a solution of 8, 245 mg (0.80 mmol) and DMAP (0.120 g, 1.6 mmol) in 20 mL CH$_2$Cl$_2$. The resulting solution was first allowed to warm to room temperature and then was heated to reflux for 40 hours. The mixture was washed with dilute HCl and brine. To the organic layer was added diethyl ether (50 mL) and the precipitate formed was collected by filtration. This crude product was purified by column chromatography using CH$_2$Cl$_2$/MeOH to give a solid. This solid was further crystallized in MeOH to yield the target molecule 1a as a white solid followed by Click reaction and deprotection of the TBS group to prepare 1b:

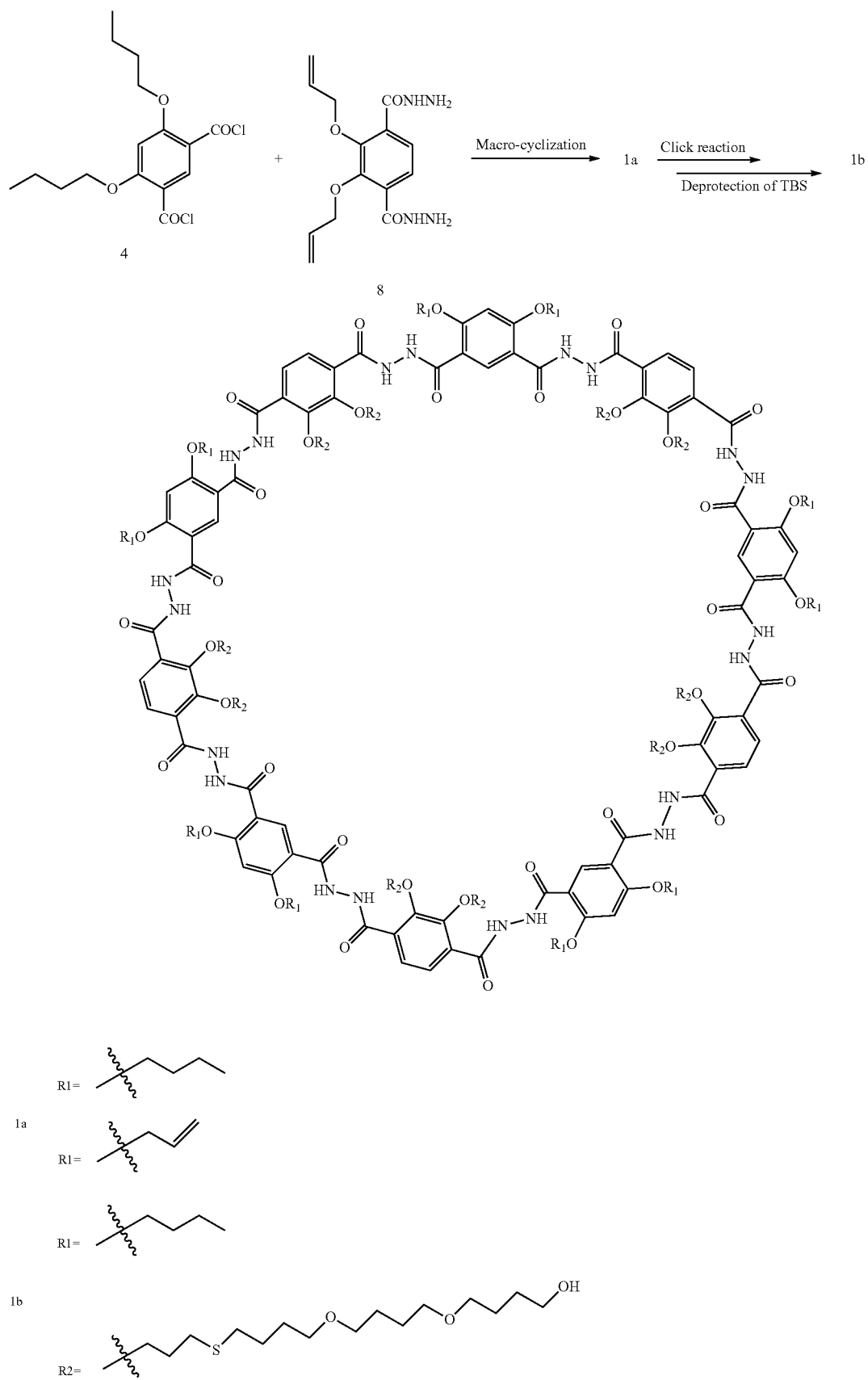

Example 4. Reduced Hemolysis with Nanopores

Synthesized nanopores were analyzed for hemolysis following red blood cell (RBC) osmotic shock.

The nanopore ring was synthesized as in Examples 1-3. Five percent of RBCs were then incubated with (black bars, on left) or without nanopores (gray bars, on right) at 10 uM that were diluted from 1 mM stock at 37° C. for 5, 10, or 15 minutes. RBCs were washed twice and subjected to 50 mM osmotic shock (re-suspend in 100 mM KCl solution) at 37° C. for 30 minutes. RBCs were centrifuged and supernatant was measured for hemoglobin content at an absorbance of 540 nM.

Referring to FIG. 2, there is reduced hemolysis when RBCs were incubated with the nanopores as compared to without the nanopores. This shows that nanopores facilitate ion transport and protects RBCs from hypotonic treatment.

Example 5. Reduced Osmotic Shock with Nanopores

Synthesized Nanopores were analyzed for swelling following RBC osmotic shock.

The nanopores were synthesized as in Examples 1-3. RBC membrane was re-suspended in 150 mM KCl solution and sonicated to generate RBC vesicles. The nanopore was added to the RBC vesicles and incubated at 37° C. The vesicles were then serially diluted in water to generate osmotic shock at 0, 10, 20, 30, or 40 mM. Size was measured immediately using dynamic light scattering.

As seen in FIG. 3, there was reduced swelling in RBC vesicles that were treated with the nanopore. This shows that nanopores facilitate ion transport and protects RBC vesicles from swelling in a hypotonic solution.

Example 6. Nanopores Facilitate Transport into RBCs

The transport of small molecules across a membrane was analyzed with synthesized nanopores.

The nanopores were synthesized as in Examples 1-3. RBCs were incubated with 2.5, 5, or 10 uM of nanopores or without nanopores at 37° C. for 10 minutes. RBCs were then washed twice. Small molecules Ciprofloxacin (FIG. 4A) and Rhodamine B (FIG. 4B) were added to RBC suspensions and incubated at 37° C. for 1 hour. RBCs are washed twice and followed by sonication. Fluorescence was detected for each small molecule.

Referring to FIG. 4A and FIG. 4B, there is increasing fluorescence as concentration of nanopores increases. This example shows that nanopores facilitate faster small molecule transport in RBCs.

Example 7: Measuring Nanopore Function

The function of synthesized nanopores is measured.

The nanopores were synthesized as in Examples 1-3. RBCs are incubated with 10 uM of nanopores at 37° C. for 10 minutes. RBCs are then washed twice. The pH-sensitive dye, 8-hydroxypyrene-1, 3, 6-trisulfonate (HPTS) is added to RBC suspensions and incubated at 37° C. for 1 hour. RBC suspensions are then subjected to an extravesicular pulse of HCl. Triton X-100, a nonionic surfactant, is used as a control.

Fluorescence emission and single channel conductance across planar lipid bilayers are measured.

Example 8: Nanopores Facilitate Transport of Nucleic Acids for Sequencing

A DNA sequence is analyzed following transport across a nanopore.

The cis and trans chambers of an apparatus are separated by a 25-um thick Teflon partition, a lipid bilayer, or a modified cell membrane. The electrolyte in both chambers is 2 M KCl and 10 mM potassium phosphate buffer (pH 7.4). A bilayer from RBCs is formed across a 60-um wide aperture in the partition. The nanopores are synthesized as in Examples 1-3 and added to the cis chamber to give a final concentration of 10 uM. An electrode is coupled to an electrical circuit that generates an electrical signal as it detects the passage of a DNA sample through or in proximity to the nanopore. Single channel recordings are taken by using a patch clamp amplifier connected to Ag/AgCl electrodes through agar bridges. The cis chamber is grounded and a positive current represents positive charge moving from the trans to cis side. A computer system is set up for data acquisition. The signal is low-pass-filtered with an 8-pole Bessel filter at a frequency of 20 kHz and is sampled at 50 kHz. A nucleic acid sequence of the DNA sample can then be generated.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A composition comprising a nanopore of Formula I, wherein Formula I is

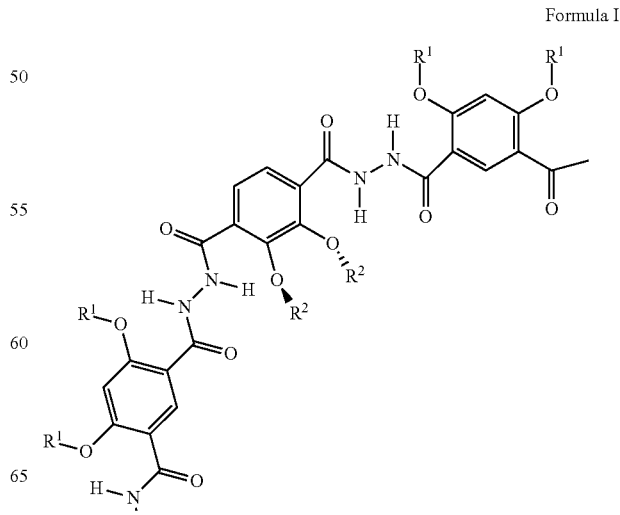

Formula I

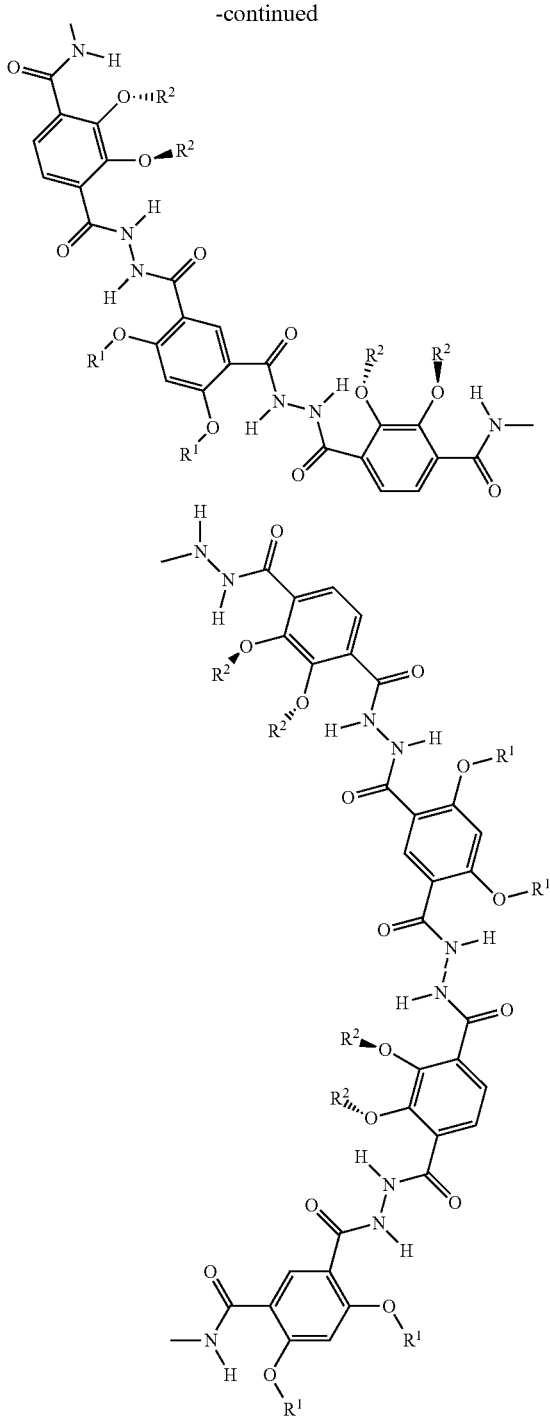

wherein: R$^1$ is —CH$_2$CH$_2$CH$_2$CH$_3$; R$^2$ is —CH$_2$CH=CH$_3$ or —(CH$_2$)$_3$S(CH$_2$)$_4$O(CH$_2$)$_4$O(CH$_2$)$_4$OH.

2. The composition of claim 1, wherein 2 or more nanopores are stacked together to form a nanotube.

3. The composition of claim 2, wherein formation of the nanotube is dependent on at least one of temperature, solvent, and concentration.

4. The composition of any one of claims 1-3, wherein a diameter of a cavity of the nanopore is in a range of about 0.5 nm to about 3 nm.

5. The composition of claim 1, wherein a diameter of a cavity of the nanopore is about 2 nm.

6. A method of detecting a target molecule, the method comprising:
 a. contacting the target molecule with a membrane comprising the composition of claim 1, wherein the nanopore of the composition has a non-collapsible cavity; and
 b. measuring an electrical stimulus across the membrane, wherein transport of the target molecule causes a change in the electrical stimulus.

7. The method of claim 6, wherein the membrane is a lipid bilayer.

8. The method of claim 7, wherein the lipid bilayer is from a cell.

9. The method of claim 8, wherein the cell is a red blood cell.

10. The method of any one of claims 6-9, wherein the electrical stimulus is at least one of applied current and an applied voltage.

11. The method of any one of claims 6-9, wherein the target molecule is at least one of RNA, DNA, and a peptide.

12. The method of claim 6, wherein the transport of the target molecule is through the cavity.

13. The method of claim 6, wherein the transport of the target molecule is in proximity to the nanopore.

14. The method of claim 6, wherein the transport of a subunit of the target molecule is measured.

15. The method of claim 14, wherein the subunit of the target molecule is a nucleotide.

16. The method of claim 6, further comprising the step of generating a sequence of the target molecule.

17. A method for making a nanopore for use in detecting a target molecule, the method comprising:
 a. providing a reactant of Formula II,

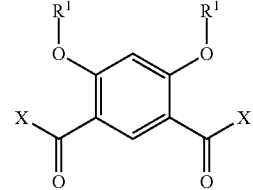

Formula II b. providing a reactant of Formula III; and

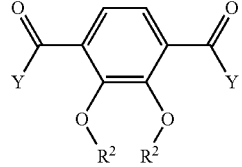

Formula III c. combining the reactant of Formula II and the reactant of Formula III to yield a product comprising the composition of claim 1;
 wherein: R$^1$ is —CH$_2$CH$_2$CH$_2$CH$_3$; X is Cl; R$^2$ is —CH$_2$CH=CH$_3$ or —(CH$_2$)$_3$S(CH$_2$)$_4$O(CH$_2$)$_4$O(CH$_2$)$_4$OH; Y is NHNH$_2$.

18. A method of at least one of drug development screening, disease diagnosis, phylogenetic classification, parental and forensic identification, disease onset and recurrence, individual response to treatment versus population bases, and monitoring of therapy using the composition of claim 1 or the method of claim 6.

19. A method of sequencing the target molecule at point of care using the composition of claim 1 or the method of claim 6.

* * * * *